(12) United States Patent
Kleyman et al.

(10) Patent No.: US 12,048,470 B2
(45) Date of Patent: Jul. 30, 2024

(54) LIGHTED ELECTROCAUTERY BLADE ASSEMBLY FOR HANDHELD ELECTROSURGICAL INSTRUMENT

(71) Applicant: Pathy Medical, LLC, Shelton, CT (US)

(72) Inventors: Gennady Kleyman, Brooklyn, NY (US); Mikiya Silver, New Haven, CT (US); Vinod V. Pathy, Shelton, CT (US)

(73) Assignee: Pathy Medical, LLC, Shelton, CT (US)

( * ) Notice: Subject to any disclaimer, the term of this patent is extended or adjusted under 35 U.S.C. 154(b) by 532 days.

(21) Appl. No.: 16/739,374

(22) Filed: Jan. 10, 2020

(65) Prior Publication Data

US 2021/0212748 A1 Jul. 15, 2021

(51) Int. Cl.
| | |
|---|---|
| *A61B 18/14* | (2006.01) |
| *A61B 18/12* | (2006.01) |
| *A61B 18/00* | (2006.01) |
| *A61B 90/30* | (2016.01) |

(52) U.S. Cl.
CPC ...... *A61B 18/1206* (2013.01); *A61B 18/1402* (2013.01); *A61B 2018/00178* (2013.01); *A61B 2018/00595* (2013.01); *A61B 2018/00601* (2013.01); *A61B 2018/1226* (2013.01); *A61B 2018/1412* (2013.01); *A61B 90/30* (2016.02); *A61B 2090/309* (2016.02)

(58) Field of Classification Search
CPC ..... A61B 90/35; A61B 90/30; A61B 18/1206; A61B 18/1402; A61B 2018/00178; A61B 2018/00595; A61B 2018/00601; A61B 2018/1226; A61B 2018/1412; A61B 2090/309
See application file for complete search history.

(56) References Cited

U.S. PATENT DOCUMENTS

| | | | |
|---|---|---|---|
| 6,562,032 B1 | 5/2003 | Ellman et al. | |
| 9,851,060 B2 | 12/2017 | Pathy | |
| 10,456,190 B2 | 10/2019 | Vayser et al. | |
| 2006/0293655 A1* | 12/2006 | Sartor | A61B 18/1402 606/49 |
| 2009/0054890 A1 | 2/2009 | DeCarlo | |

(Continued)

FOREIGN PATENT DOCUMENTS

| | | |
|---|---|---|
| CN | 209548080 U | 10/2019 |
| EP | 2027824 B1 | 2/2009 |

OTHER PUBLICATIONS

PCT International Search Report and Written Opinion dated May 10, 2021, issued during the prosecution of PCT International Patent Application No. PCT/US2021/012478.

*Primary Examiner* — Sean W Collins
(74) *Attorney, Agent, or Firm* — Locke Lord LLP; Scott D. Wofsy

(57) ABSTRACT

A lighted electrocautery blade assembly is disclosed for attachment to a handheld electrosurgical instrument, which includes a housing having an LED light assembly at a distal end thereof for illuminating a surgical site, and an electrode operatively associated with the housing and including a distal portion defining an electrocautery blade and a proximal portion defining a connector for electrically coupling with an electrosurgical instrument.

6 Claims, 32 Drawing Sheets

(56) References Cited

U.S. PATENT DOCUMENTS

| | | | |
|---|---|---|---|
| 2012/0101497 A1* | 4/2012 | Jayaraj | A61B 90/13 606/45 |
| 2012/0221000 A1 | 8/2012 | Bromley et al. | |
| 2013/0197317 A1* | 8/2013 | Daniel | A61B 1/0684 600/249 |
| 2014/0293590 A1* | 10/2014 | Pathy | F21L 4/02 362/184 |
| 2016/0157920 A1* | 6/2016 | Vayser | A61B 18/1402 600/249 |
| 2019/0380805 A1* | 12/2019 | Greeley | A61B 90/30 |

* cited by examiner

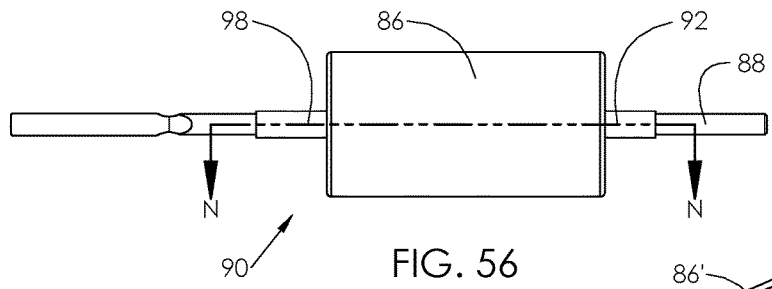
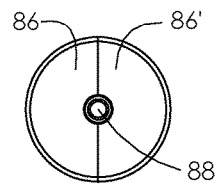
FIG. 56   FIG. 57
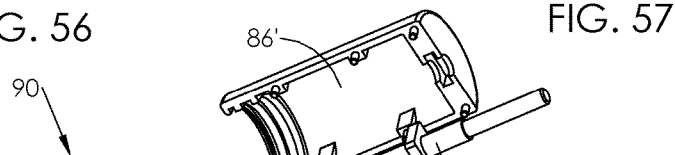
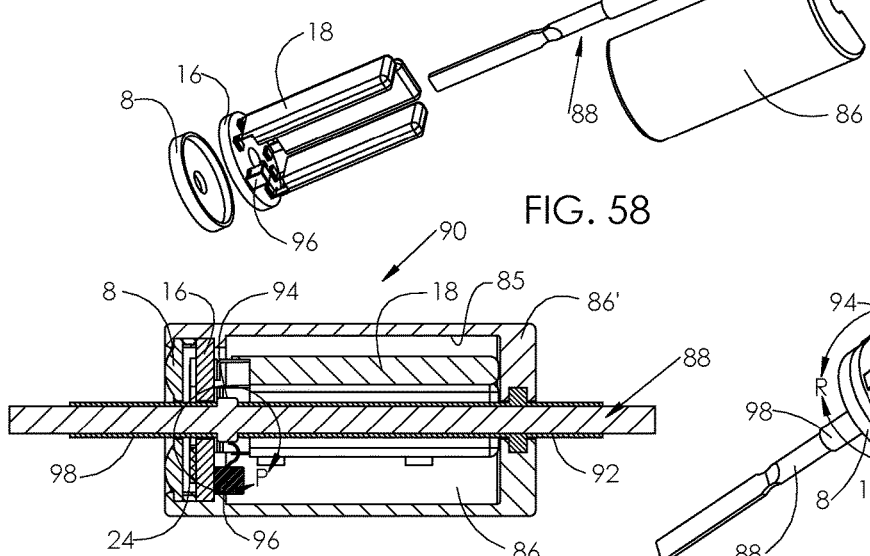
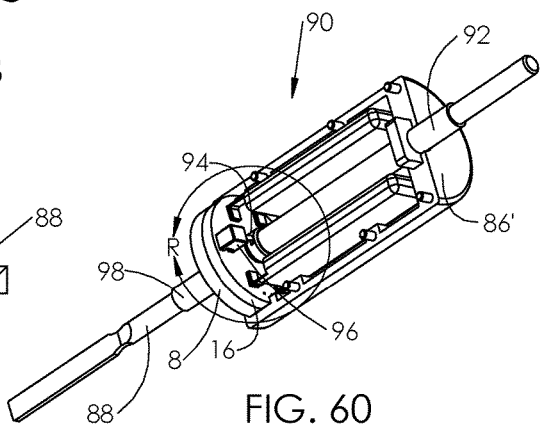
FIG. 58   FIG. 59   FIG. 60
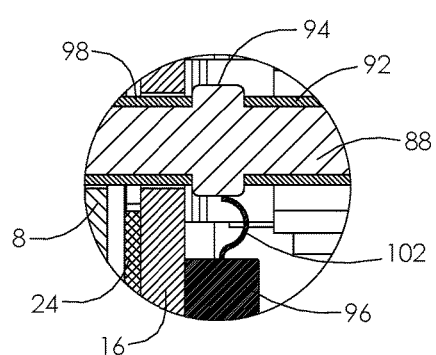
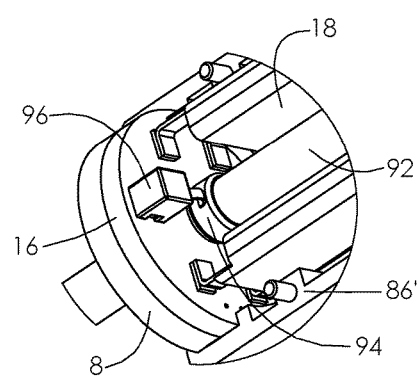
FIG. 61   FIG. 62

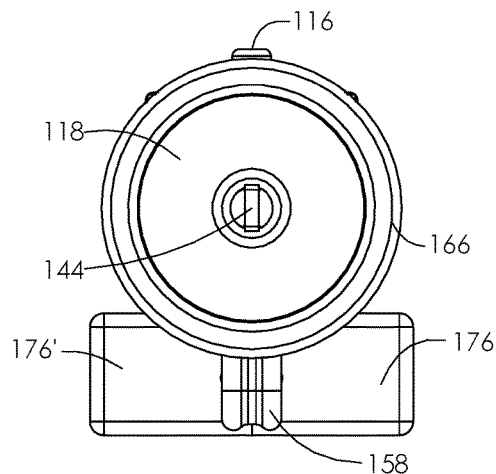
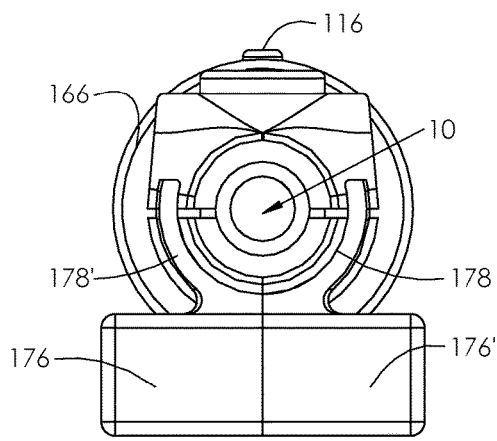
FIG. 92　　　　FIG. 93
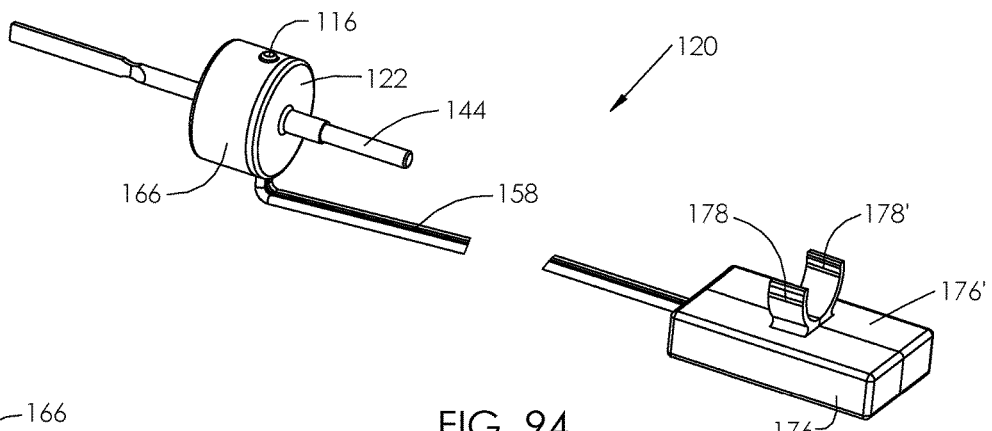
FIG. 94
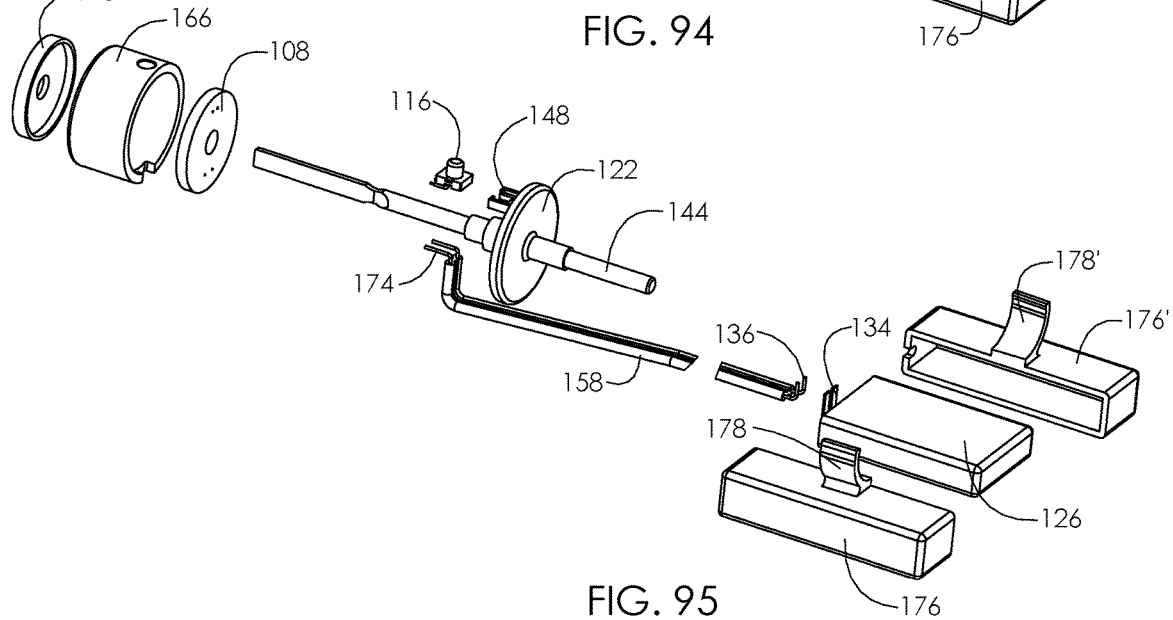
FIG. 95

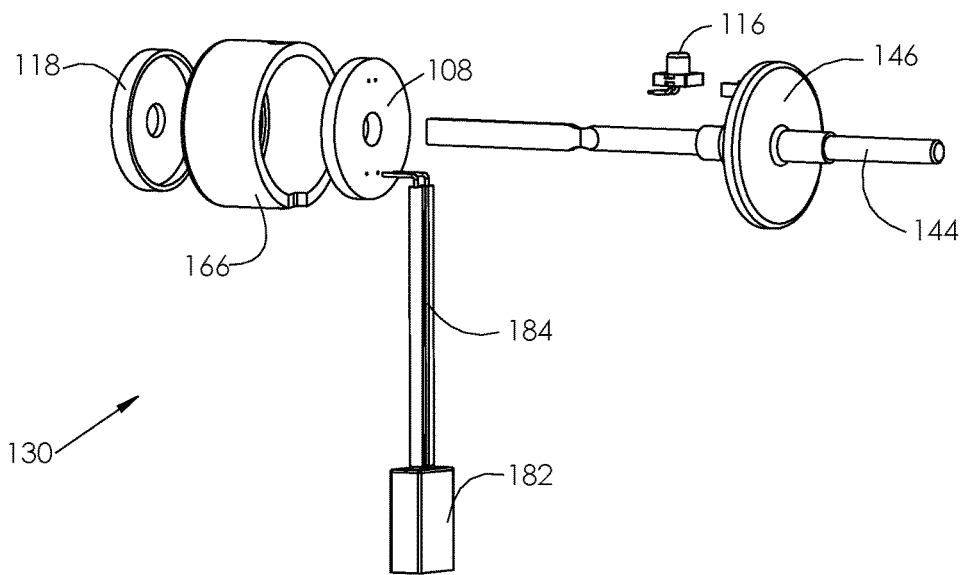
FIG. 101
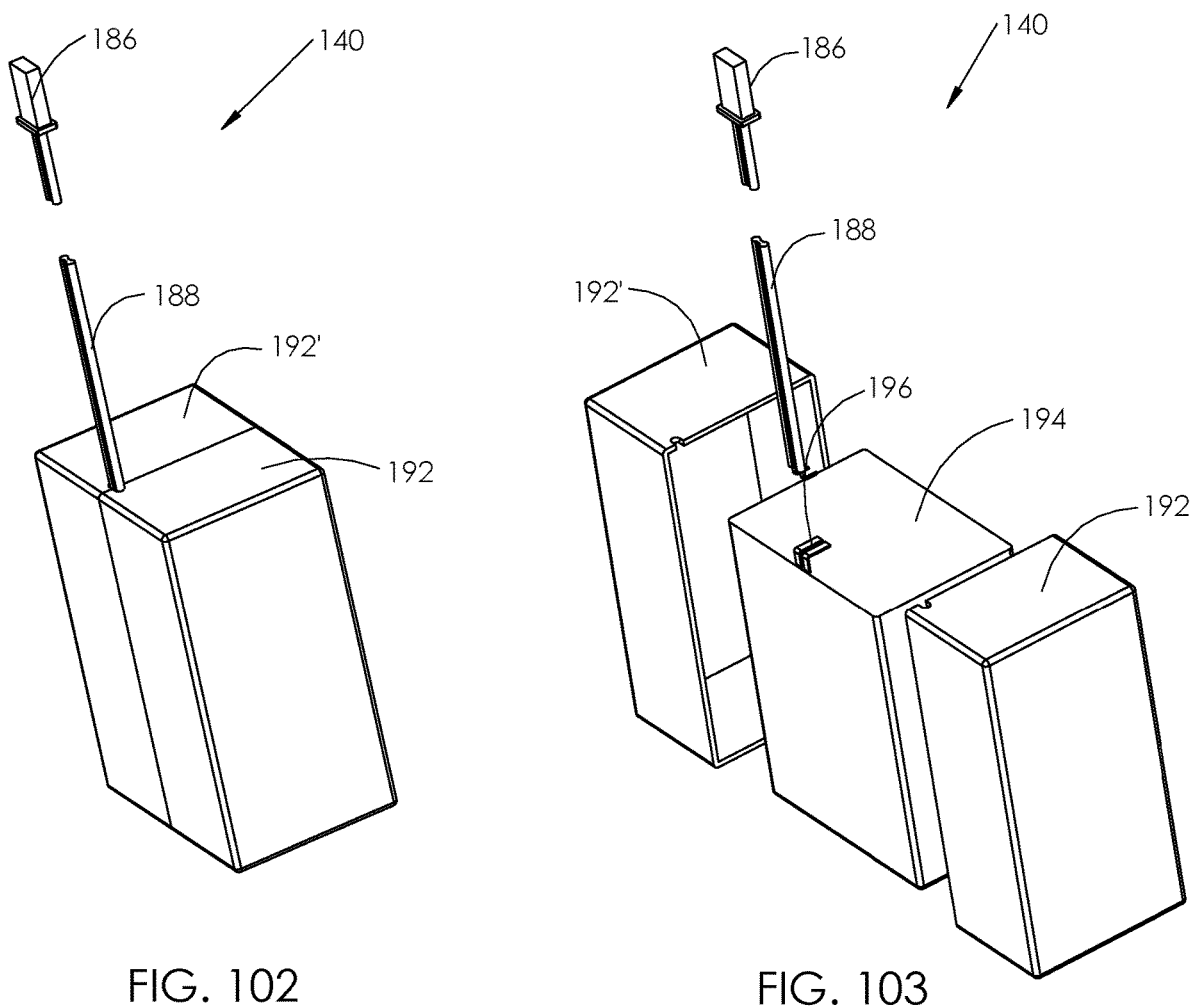
FIG. 102
FIG. 103

őLIGHTED ELECTROCAUTERY BLADE ASSEMBLY FOR HANDHELD ELECTROSURGICAL INSTRUMENT

BACKGROUND OF THE INVENTION

1. Field of the Invention

The subject invention is directed to surgical instrumentation, and more particularly, to a lighted electrocautery blade assembly for use with a handheld electrosurgical instrument.

2. Description of Related Art

In medical practice, lighting devices are used to direct light at a specific area being operated on or examined by a surgeon. For example, lighting devices can be used in conjunction with a handheld electrosurgical device, such as a BOVIE® pencil, which is typically used to incise tissue during a surgical procedure.

Some instruments known in the art include an integral light source, but these devices are generally expensive and relatively bulky. Cordless and corded lighting devices for surgical tools are also known in the art, but these can also add bulk, preventing a user from manipulating the tool with precision or in confined spaces.

Additionally, many lighting devices, especially corded devices and overhead lights, require constant repositioning, are assistant-dependent to hold or re-position, and can be disruptive to a surgical field. Furthermore, corded lighting devices, as well as light sources that are integrated into a tool can become hot, burning the user and/or patient, and possibly even causing a fire.

Headlights can be used as an alternative to a lighting device during a surgical procedure. However, similar to lighting devices, headlights are bulky, commonly require cables to connect to a power source, require constant readjustment, and can pose a potential safety hazard. Moreover, being worn on the head of the surgeon, they are at a distance from the surgical field, decreasing their effectiveness, and they can cause fatigue and strain if worn for an extended period of time.

It is known that when handheld lighting devices, overhead lights and/or headlamps are employed during a surgical procedure, the hands/tools of the surgeon can block the light and cast a shadow on the surgical site, which is undesirable. Those shadows require the user to reposition the lighting sources regularly, and can even require the surgeon to move their head to try to angle the headlamp towards the surgical site differently.

A particularly useful battery powered lighting device designed for attachment to a handheld electrosurgical device, and in particular, for use with an electrocautery pencil, is disclosed in commonly assigned U.S. Pat. No. 9,851,060, the disclosure of which is herein incorporated by reference in its entirety. This device overcomes the deficiencies of the prior art lighting devices described above. However, there is still room in this art for improvement, and the subject invention is directed to several of those improvements, including a lighted electrocautery blade assembly for use with a handheld electrosurgical instrument.

SUMMARY OF THE DISCLOSURE

The subject invention is directed to new and useful lighting devices for installation on a handheld surgical instrument, and preferably, for releasable attachment to a handheld electrosurgical instrument. More particularly, the subject invention is directed to a lighted electrocautery blade assembly for releasable attachment to a handheld electrosurgical instrument.

One embodiment of the subject invention is directed to a lighted electrocautery blade assembly that includes an elongated housing having an LED light assembly at a distal end thereof for illuminating a surgical site, and an electrode that extends through and is mounted within the elongated housing such that a distal end portion of the electrode extends from the distal end of the elongated housing to define an electrocautery blade and a proximal end portion of the electrode extends from the proximal end of the elongated housing to define a connector for electrically coupling with an electrosurgical instrument.

The LED light assembly preferably surrounds the electrocautery blade and is powered by a first energy source, and the electrode is powered by a second energy source that is separate and distinct from the first energy source. The first energy source consists of at least one battery cell supported within the elongated housing and the second energy source is a source of RF energy that is connected to the electrosurgical instrument. Preferably, the first energy source is defined by a plurality of battery cells that are supported within the elongated housing. It is envisioned hat the first energy source could be charged by the second energy source. The first energy source can be an external source of electrical power to which the LED light assembly is connected by way of a power cord.

Preferably, the first energy source is controlled by a switch that is operatively associated with the elongated housing and is connected to a contact boss formed on the electrode. The switch can be located on an outer peripheral surface of the housing for manual actuation by a surgeon, or it can be located on a proximal surface of the elongated housing to interact with a distal end portion of the electrosurgical instrument when the electrocautery blade assembly is attached thereto.

Preferably, a medial portion of the electrode is sheathed in an over-molded electrically insulating sleeve and a rectangular flange is provided on the medial portion of the electrode for engaging a complementary recess formed within the housing for securely mounting the electrode within the housing. The proximal end portion of the electrode may be conically tapered or slotted to facilitate or otherwise accommodate the releasable attachment of the blade assembly to different sized, types or brands of electrosurgical instruments.

The LED light assembly includes a plurality of LED light sources that are supported on a printed circuit board, and a lens is positioned within the housing in front of the LED light assembly. The lens can include a continuous annular lens surface or it can include a non-continuous lens surface having plural convex light focusing lens surfaces. It is envisioned that these lens surfaces could be tuned to focus light for use with a particular blade length.

The subject invention is also directed to a lighted electrocautery blade assembly for attachment to a handheld electrosurgical instrument, which includes an elongated housing having an LED light assembly at a distal end thereof for illuminating a surgical site, and an electrode adapter operatively associated with the elongated housing and including a distal reception portion operatively associated with the distal end of the housing for receiving a detachable electrocautery blade, a medial body portion supported with the elongated housing and a proximal connector portion extending from a proximal end of the elongated housing for electrically coupling with an electrosurgical instrument. The distal reception portion of the electrode adapter can extend from the distal end of the elongated housing to receive a detachable electrocautery blade, or it can be located within the elongated housing adjacent the distal end thereof to receive a detachable electrocautery blade.

The subject invention is also directed to a lighted electrocautery blade assembly for attachment to a handheld electrosurgical instrument that includes an elongated housing having an LED light assembly at a distal end thereof for illuminating a surgical site, and an electrode operatively associated with the housing that includes a distal blade portion extending from the distal end of the housing and a proximal connector portion extending from a proximal end of the housing for electrically coupling with an electrosurgical instrument, wherein the LED light assembly is powered by an external battery pack that is contained within a battery housing.

The battery housing may be connected to the elongated housing of the blade assembly by way of an elongated connective cable, and an elongated linkage beam can extend between the battery housing and the elongated housing to support the elongated connective cable. Alternatively, the battery housing can include clasping means for attaching the battery housing to a proximal end portion of the electrosurgical instrument, or it can include clasping means for attaching the battery housing to the RF power cable associated with the electrosurgical instrument.

The subject invention is also directed to a kit for performing a surgical procedure, which includes a packaging enclosure, a handheld electrosurgical instrument within the packaging enclosure and configured for connection to a source of RF energy, and a lighted electrocautery blade assembly within the packaging enclosure for attachment to the handheld electrosurgical instrument and powered by at least one internal battery cell. The kit can further include a plurality of electrocautery blades for use with the electrocautery blade assembly. The electrocautery blades can have similar tip configurations or one or more of the electrocautery blades can have different functional tip configurations.

These and other features of the lighting blade assembly of the subject invention will become more readily apparent to those having ordinary skill in the art to which the subject invention appertains from the detailed description of the preferred embodiments taken in conjunction with the following brief description of the drawings.

BRIEF DESCRIPTION OF THE DRAWINGS

So that those skilled in the art will readily understand how to make and use the lighted electrocautery blade assembly of the subject invention without undue experimentation, preferred embodiments thereof will be described in detail herein below with reference to the figures wherein:

FIG. 56 is a side elevational view of the lighted blade assembly of FIG. 54;

FIG. 57 is a front elevational view of lighted blade assembly of FIG. 54;

FIG. 58 is an exploded perspective view of the lighted blade assembly of FIG. 54;

FIG. 59 is a cross-sectional view taken along line N-N of FIG. 56;

FIG. 60 is a perspective view of the lighted blade assembly of FIG. 54 with a portion of the body removed to illustrate the interior components thereof;

FIG. 61 is an enlarged localized view of area P taken from FIG. 59;

FIG. 62 is an enlarged localized view of area R taken from FIG. 59;

FIGS. 92 and 93 are front and back elevational views of the instrument and lighted blade assembly of FIG. 89;

FIG. 94 is a perspective view of the lighted blade assembly of FIG. 88;

FIG. 95 is an exploded perspective view of the lighted blade assembly of FIG. 88;

FIG. 101 is an exploded perspective view of the lighted blade assembly of FIG. 96;

FIG. 102 is a perspective view of the battery assembly shown in FIG. 98;

FIG. 103 is an exploded perspective view of battery assembly of FIG. 102;

DETAILED DESCRIPTION OF THE PREFERRED EMBODIMENTS

Figure 1:
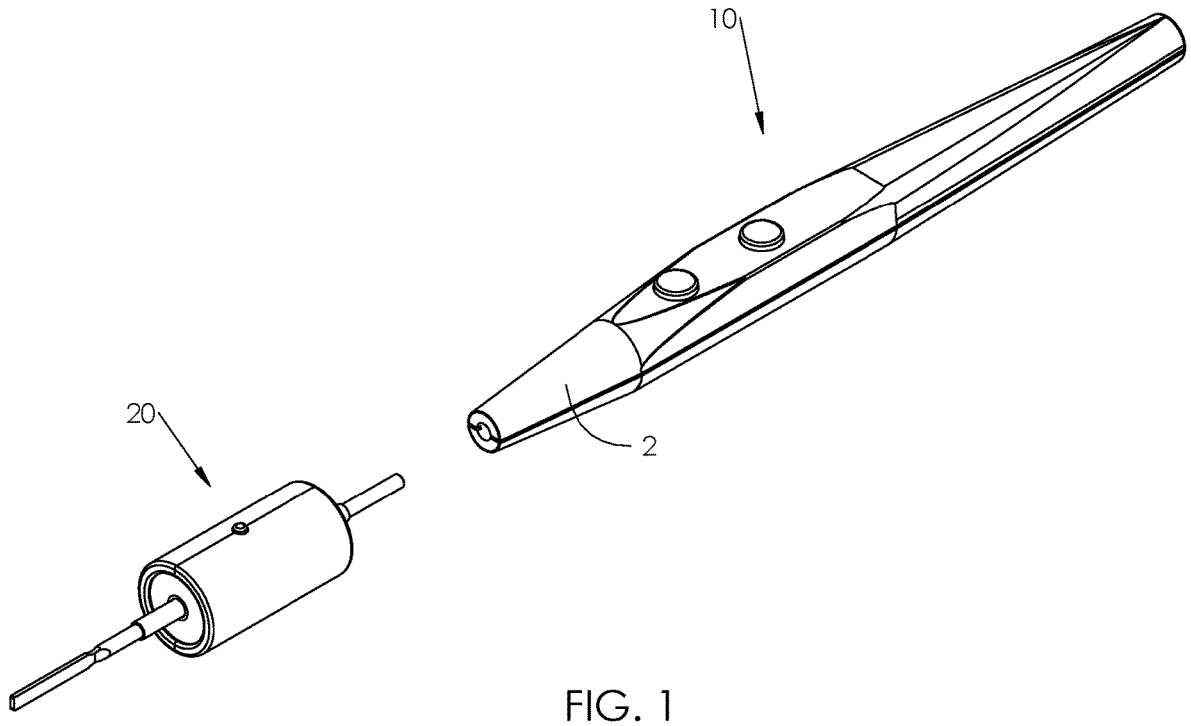
FIG. 1 is a perspective view of a lighting blade assembly separated from surgical instrument to which it may be attached.
Figure 2:
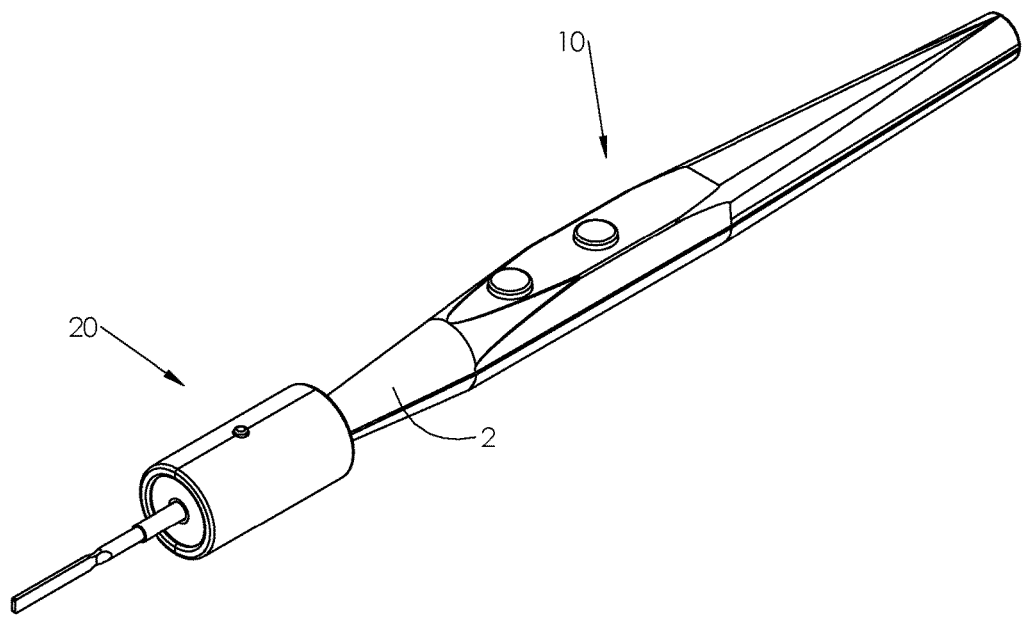
FIG. 2 is a perspective view of the lighted blade assembly attached to the surgical instrument shown in FIG. 1.
Figure 3:
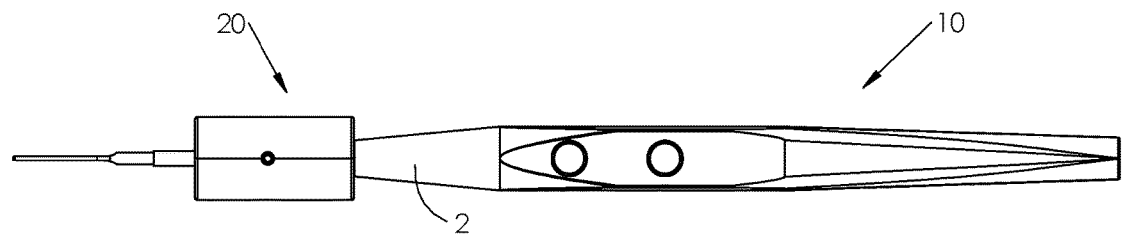
FIG. 3 is a top plan view of the lighted blade assembly attached to the surgical instrument shown in FIG. 1.
Figure 4:
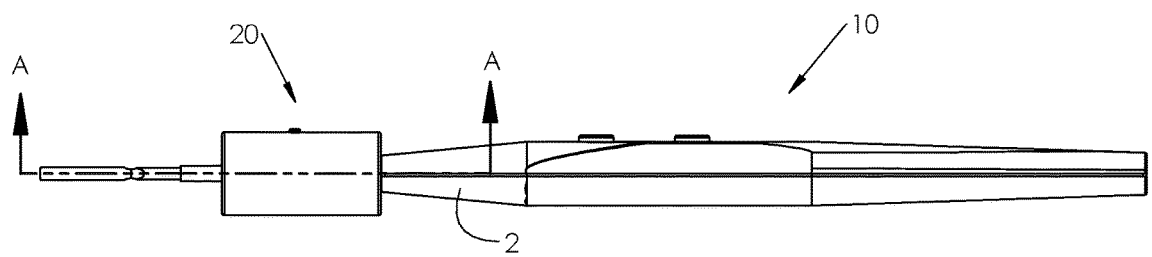
FIG. 4 is a side elevational view of the lighted blade assembly attached to the surgical instrument shown in FIG. 1.

Referring now to the drawings wherein like reference numerals identify similar structural elements or features of the various embodiments of the subject invention, there is illustrated in FIGS. 1 through 4 a first embodiment of a lighted electrocautery blade assembly designated by reference 20 that is adapted and configured for releasable attachment to the distal end portion 2 of a handheld electrosurgical instrument 10.

Figure 13:
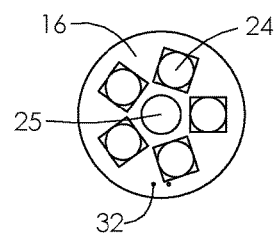
FIG. 13 is a front plan view of the PC Board, LED and battery assembly.

Referring to FIGS. 5 through 9, the lighted electrocautery blade assembly 20 includes an elongated, generally cylindrical, two-part housing 14, 14' having an LED light assembly that includes an annular printed circuit board (PCB) 16. The annular PCB 16 is installed in an annular recess 16a that is located at a distal end of the housing 14, 14' so that the LED light assembly can illuminate a surgical site. More particularly, as illustrated in FIG. 13, the annular PCB 16 includes a plurality of embedded LED's 24 that are arranged in a circumferentially spaced apart pattern surrounding a blade accommodating central aperture 25.

The embedded LEDs 24 preferably provide illumination for surgery within the visual spectrum of light. It is envisioned however, that one or more of the plurality of embedded LEDs 24 could be selected to provide UV illumination (UV-A, UV-B or UV-C) for sterilizing or otherwise treating tissue at the operative site. An annular lens 8 is preferably positioned in front of the circumferentially spaced apart LED's 24 on PCB 16 in an annular recess 8a in housing 14, 14'. As shown, the annular lens 8 include a continuous lens surface or it can include a non-continuous lens surface having a plurality of convex light focusing lens surfaces, as discussed in more detail below.

Figure 5:
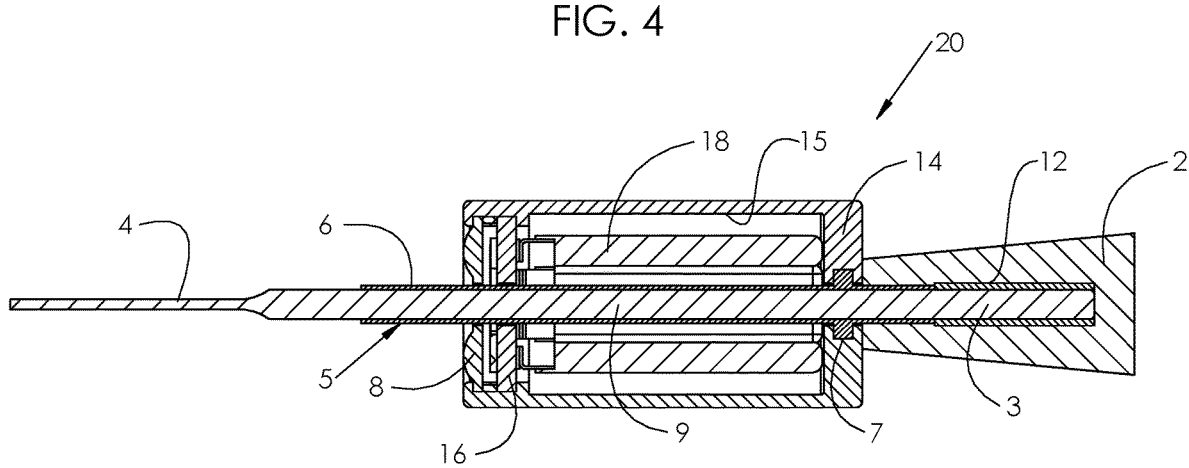
FIG. 5 is an enlarged cross-sectional view taken along line A-A of FIG. 4, showing the interior of the lighted blade assembly.
Figure 6:
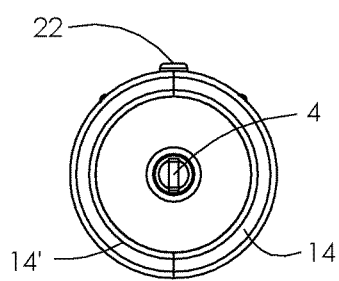
FIG. 6 is a front elevational view of the instrument with the lighted blade assembly attached thereto.
Figure 7:
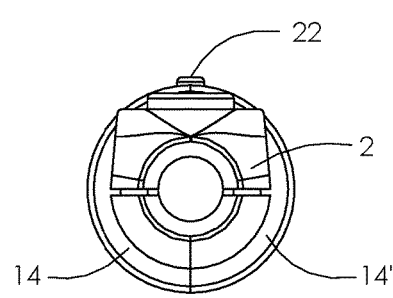
FIG. 7 is a rear elevational view of the instrument with the lighted blade assembly attached thereto.
Figure 8:
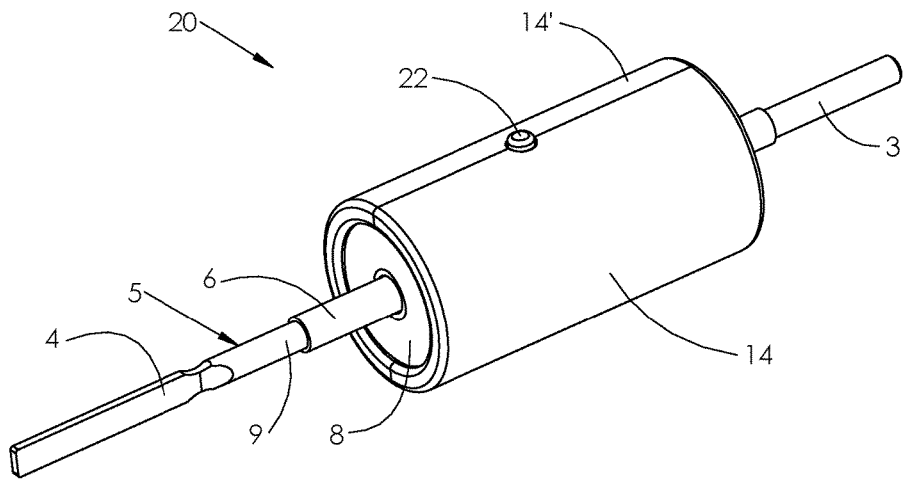
FIG. 8 is a frontal perspective view of the lighted blade assembly shown in FIG. 1.

The lighted blade assembly 20 further includes an elongated electrode 5. The electrode 5 extends through and is mounted within the interior cavity 15 of the elongated housing 14, 14' such that a distal end portion of the electrode 5 extends from the distal end of the elongated housing 14, 14' (through the central aperture 25 in PCB 16 and annular lens 8) to define an electrocautery blade 4 and a proximal end portion of the electrode 5 extends from the proximal end of the housing 14, 14' to define a connector 3 for electrically coupling with the electrosurgical instrument 10, as best seen in FIG. 5. More particularly, as shown in FIG. 5, the proximal connector 3 of electrode 5 is dimensioned and configured for coupling engagement with a complementary reception sleeve 12 in the distal end portion 2 of electrocautery instrument 10.

It is envisioned that the distal blade portion 4 of electrode 5 could have a different functional tip configuration than that which is illustrated herein. For example, the distal blade portion 4 of electrode 5 could be configured as an L hook electrode, a ball electrode, or a needle electrode, and the distal blade portion 4 could be of different lengths and widths as well. It is also envisioned that the proximal connector portion 3 of electrode 5 may be conically tapered or slotted to facilitate the attachment of the blade assembly 20 to different sized or types of electrosurgical instruments that are currently or may become available in the marketplace.

Figure 9:
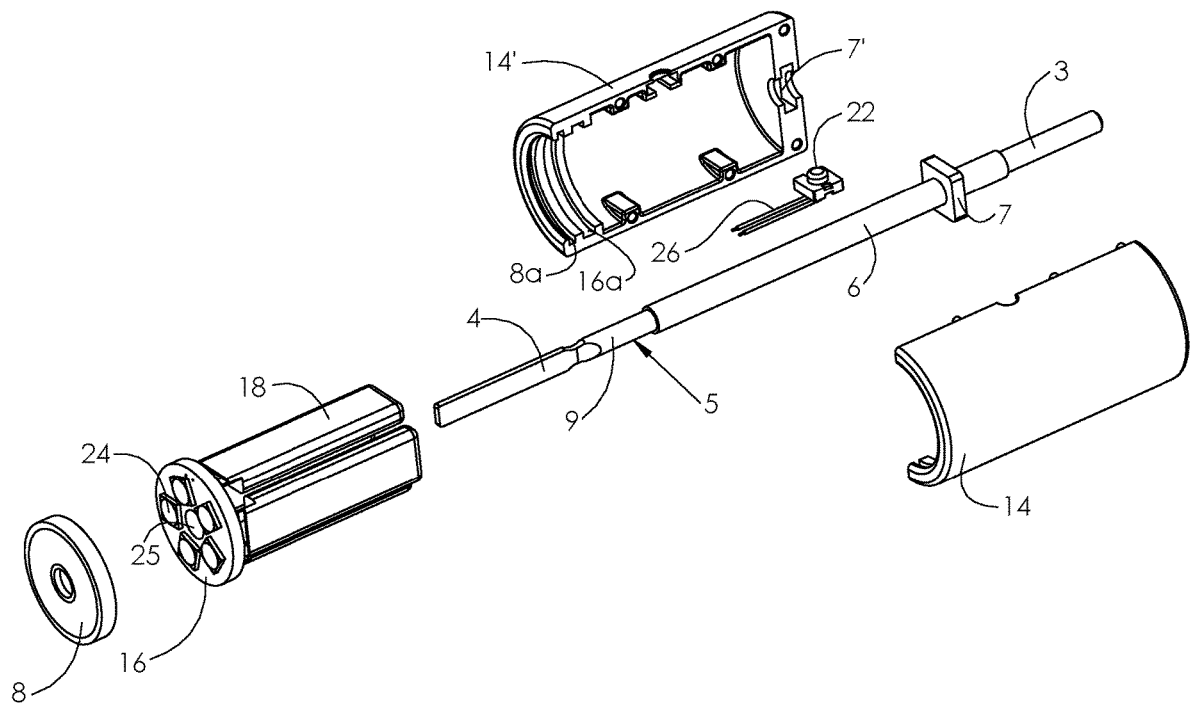
FIG. 9 is an exploded perspective view of the lighted blade assembly of FIG. 8.

Referring to FIG. 9, the LED light assembly embedded on PCB 16 surrounds the electrocautery blade 4 to provide shadow-free light directed at the surgical site. The light assembly is powered by a first energy source 18, and the electrode 5 is powered by a second energy source that is separate and distinct from the first energy source 18. The first energy source 18 consists of at least one battery cell supported within the interior cavity 15 of the elongated housing 14, 14' and the second energy source is a source of RF energy connected to the electrosurgical instrument 10. More particularly, the RF energy for the electrosurgical instrument 10 is provided by a generator (not shown) and the energy is passed through wires in the instrument to the electrode 5.

Figure 12:
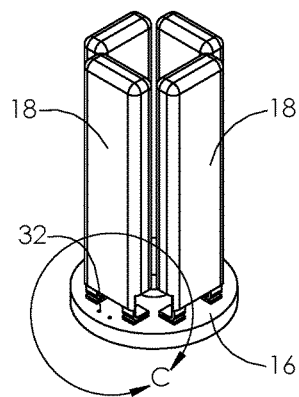
FIG. 12 is a perspective of the PC Board, LED and battery assembly.
Figure 14:
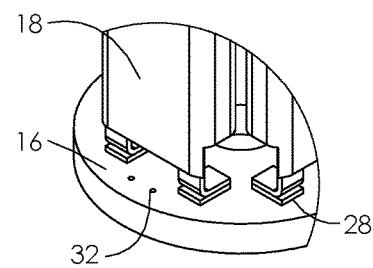
FIG. 14 is an enlarged localized view of area C taken from FIG. 12.
Figure 15:
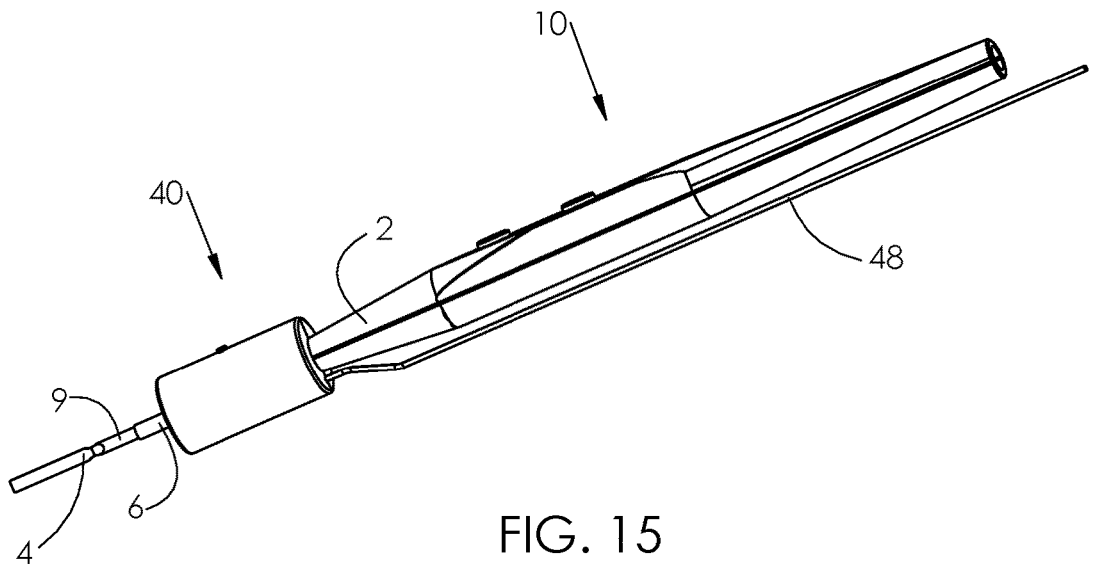
FIG. 15 is a perspective view of another embodiment of lighted blade assembly of the subject invention attached to a surgical instrument.
Figure 16:
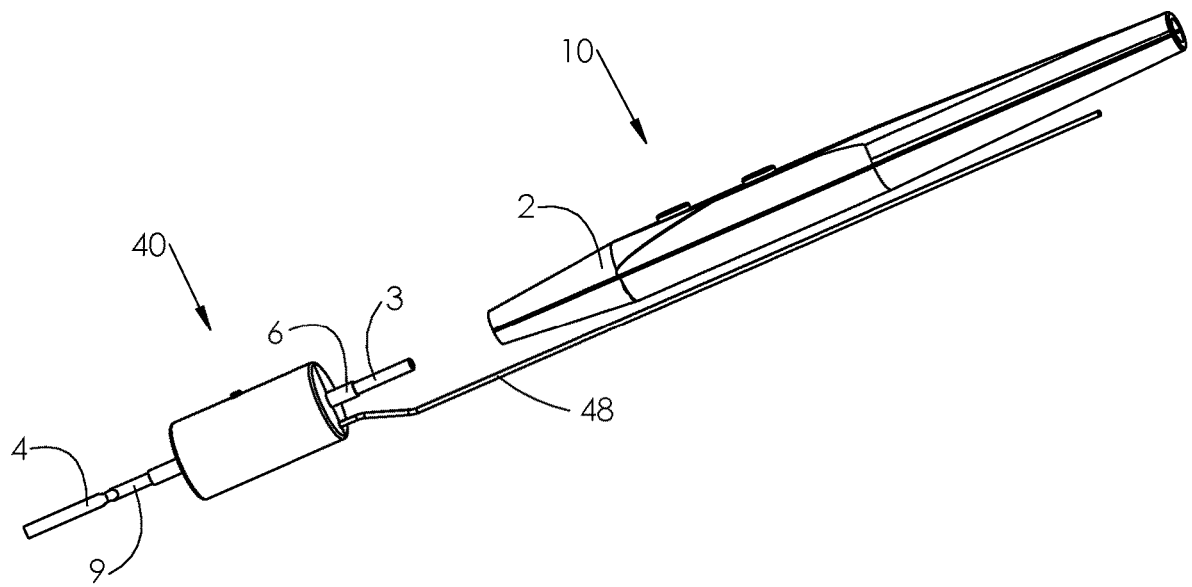
FIG. 16 is a perspective view of the lighted blade assembly of FIG. 15 separated from the surgical instrument.
Figure 17:
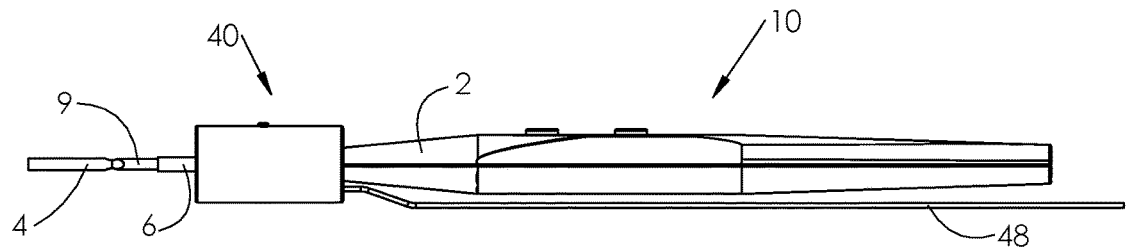
FIG. 17 is a side elevational view of the lighted blade assembly attached to a surgical instrument as shown in FIG. 16.
Figure 18:
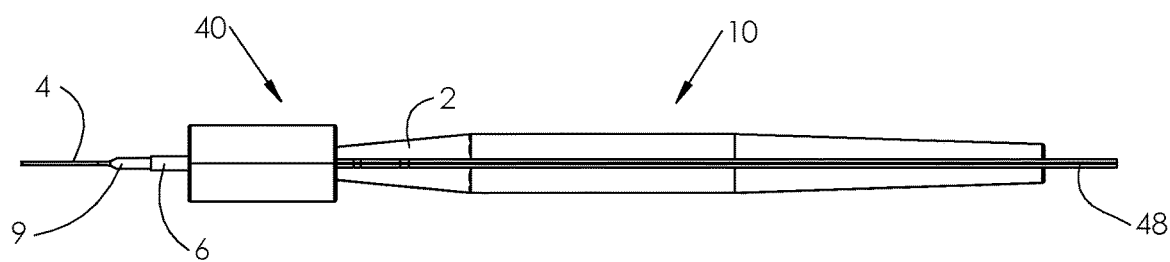
FIG. 18 is a bottom plan view of the lighted blade assembly attached to a surgical instrument as shown in FIG. 16.

Preferably, as shown in FIGS. 12 and 14, the first energy source 18 is defined by a plurality of battery cells that are supported within the interior cavity 15 of elongated housing 14, 14' and connected to contacts 28 on the proximal surface of the PCB 16. It is envisioned that the first energy source 18 may consist of a plurality of rechargeable battery cells that can be readily charged by the RF energy source that powers the electrocautery instrument 10.

Figure 10:
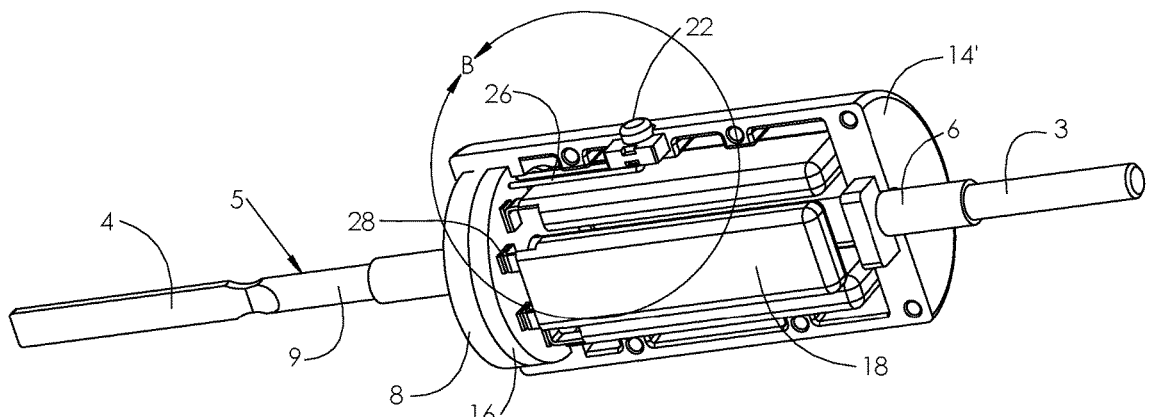
FIG. 10 is a perspective view of the lighted blade assembly with the body removed for better visibility of the interior.
Figure 11:
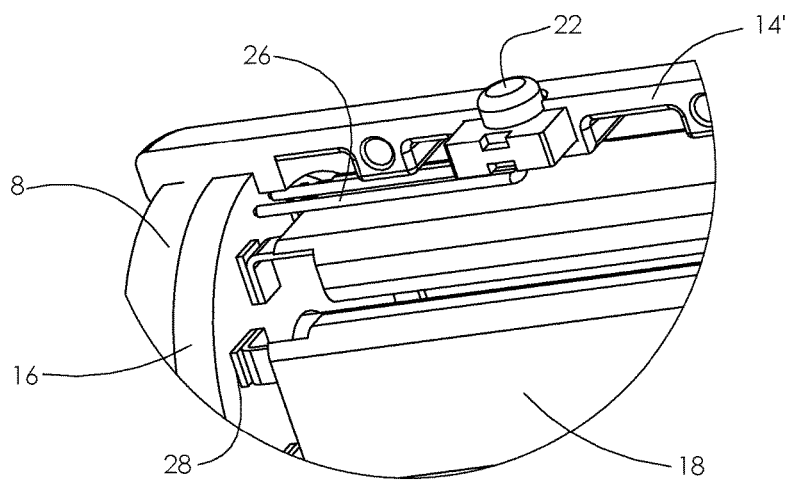
FIG. 11 is an enlarged localized view of area B taken from FIG. 10.

Referring to FIGS. 10 and 11, preferably, the first energy source 18 is controlled by a push-button actuation switch 22 that is operatively associated with the elongated housing 14, 14' and is connected to a the PCB 16 by way of electrical connections 26 that terminate at connection points 32, which are best seen in FIGS. 12 through 13. Preferably, the on-off switch 22 is located on an outer peripheral surface of the housing 14, 14' as shown for manual actuation. Alternatively, as discussed in more detail below, the push-button on-off switch can be located on a proximal surface of the elongated housing 14, 14' to interact with a distal end surface of the electrosurgical instrument 10 when the lighted electrocautery blade assembly 20 is attached thereto.

Referring to FIGS. 5 and 9, the electrode 5 includes an elongated central or medial body portion 9 that is substantially covered or otherwise sheathed in an over-molded electrically insulating sleeve 6. In addition, a rectangular flange 7 is integrally formed on the medial portion 9 of the electrode 5 for engaging a complementary recess 7' that is formed within the housing 14, 14' to securely mount the electrode 5 within the interior cavity of the housing 14, 14'. This mounting configuration advantageously prevents the axial rotation of the electrode 5 relative to the housing 14, 14' once the lighted blade assembly 20 is assembled.

Referring now to FIGS. 15 through 27B, there is illustrated another embodiment of the lighted blade assembly of the subject invention, which is designated generally by reference numeral 40. The lighted blade assembly 40 is similar to the lighted blade assembly 20 described above and illustrated in FIG. 8, but it differs in that power for the LED light assembly is provided by an external power source as opposed to a power source located within the interior of the housing of the assembly.

Figure 19:
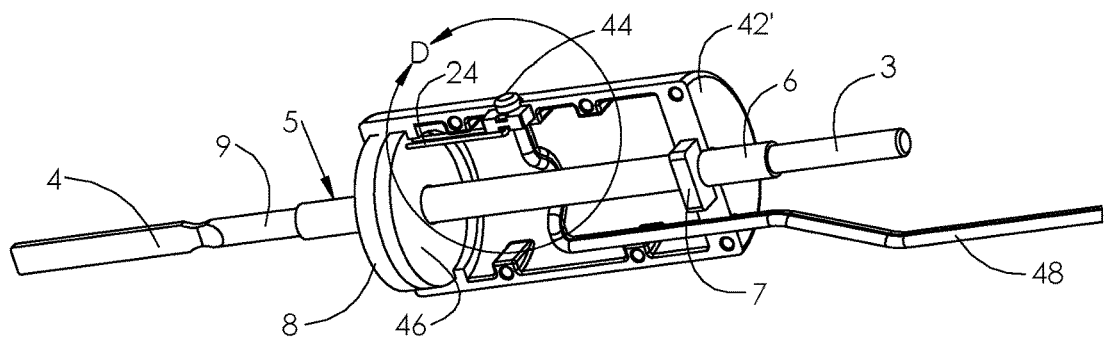
FIG. 19 is a perspective view of lighted blade assembly of FIG. 16 with the body removed for better interior visibility.
Figure 20:
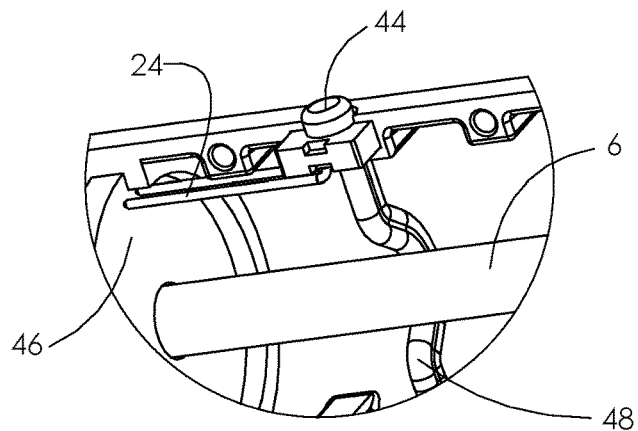
FIG. 20 is an enlarged localized view of area D taken from FIG. 19.
Figure 21:
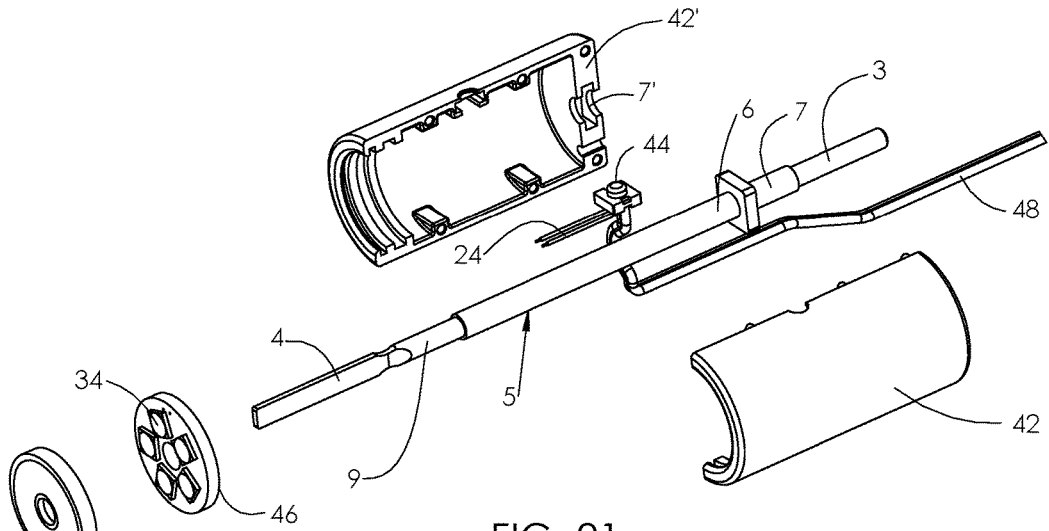
FIG. 21 is an exploded perspective view of the lighted blade assembly attached to a surgical instrument as shown in FIG. 16.
Figure 22:
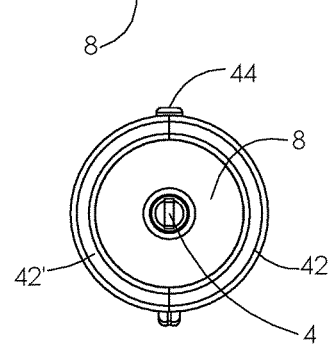
FIG. 22 is a front elevational view of the lighted blade assembly of FIG. 16.
Figure 23:
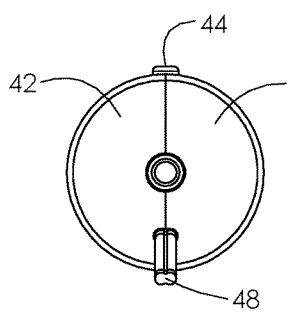
FIG. 23 is a rear elevational view of the lighted blade assembly of FIG. 16.
Figure 24:
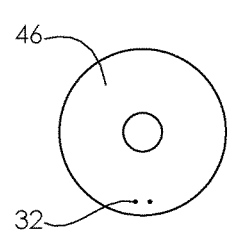
FIGS. 24-26 are rear, side and front elevational views, respectively, of the PC Board and LED assembly of the lighted blade assembly of the subject invention.
Figure 25:
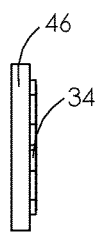
Figure 26:
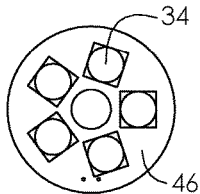

More particularly, as best seen in FIGS. 19 through 21, an elongated electrical wire 48 extends from an external power source (not shown) through a proximal wall of the housing 42, 42' to connect with a push-button actuation switch 44. The actuation switch 44 is connected by internal electrical connections 24 to the annular PCB 46 which supports a plurality of embedded LEDs 34, as best shown in FIG. 21.

Figure 27A:
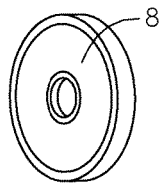
FIGS. 27A and 27B show a lens with a continuous surface for focusing the LED light.
Figure 27B:
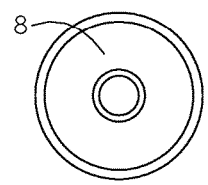
Figure 28A:
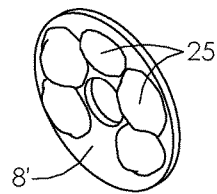
FIGS. 28A and 28B show a lens with non-continuous surfaces for focusing the LED light.
Figure 28B:
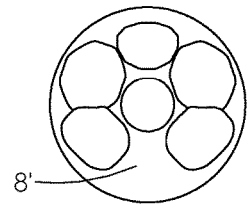
Figure 29:
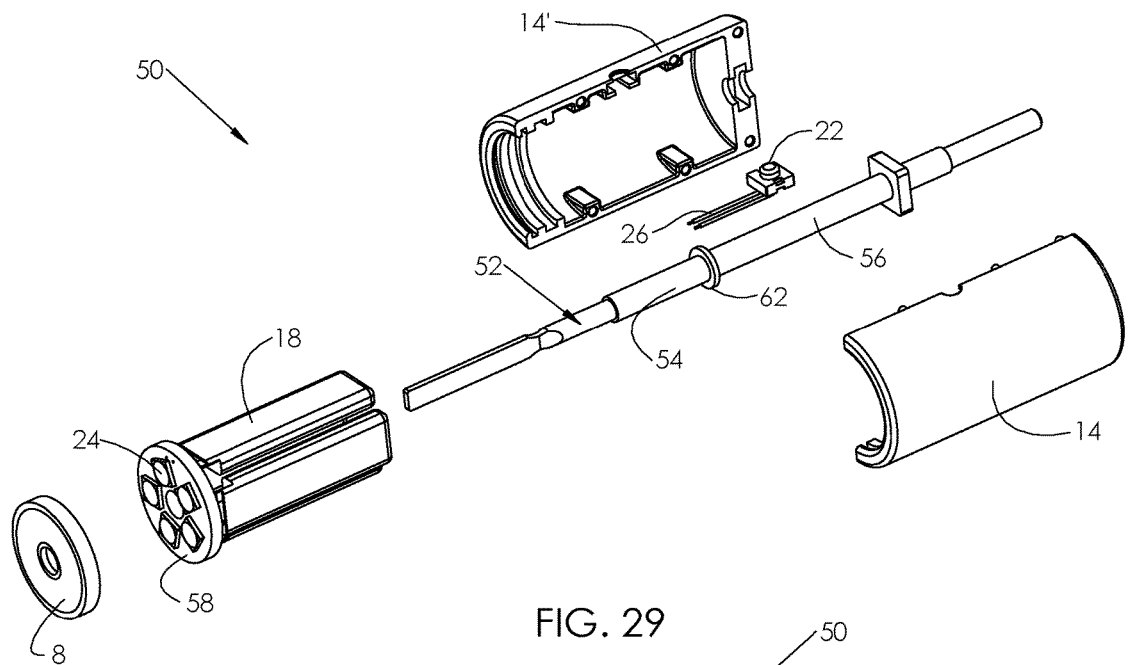
FIG. 29 is an exploded perspective view of another embodiment of the lighted blade assembly of the subject invention.
Figure 30:
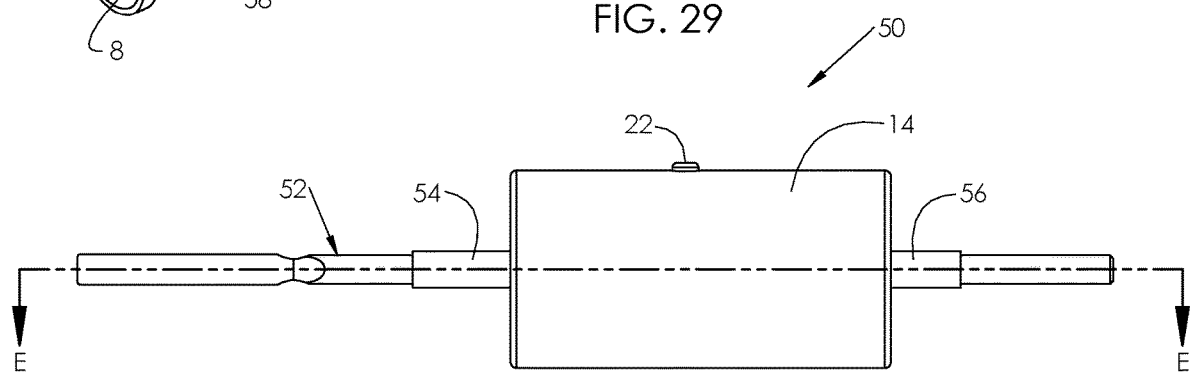
FIG. 30 is a side elevational view of the another embodiment of a lighted blade assembly.
Figure 31:
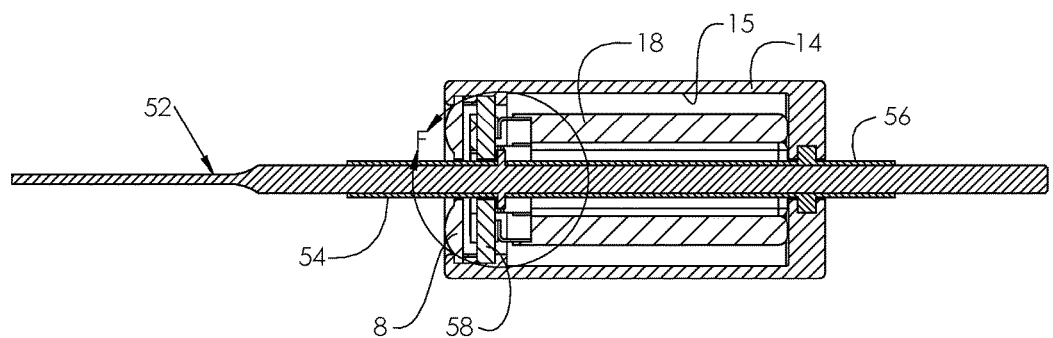
FIG. 31 is a cross-sectional view taken along line E-E of FIG. 30.

Referring now to FIGS. 28A and 28B, there is illustrated an alternative embodiment of the annular lens, which is designated by reference numeral 8' that differs from the annular lens 8 shown in FIGS. 27A and 27B, in that it includes a plurality of convex lens surfaces 25, as opposed to a continuous annular lens surface. The convex lens surfaces 25 are designed to focus light emanating from the LEDs 24 embedded in PCB 16 toward the axis of the distal blade portion 4 of the elongated electrode 5.

Figure 32:
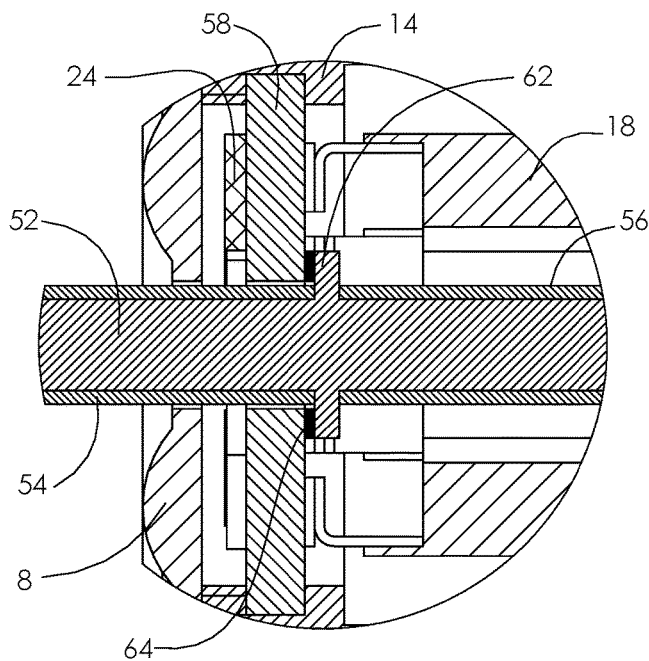
FIG. 32 is an enlarged localized view of area F taken from FIG. 31.
Figure 33:
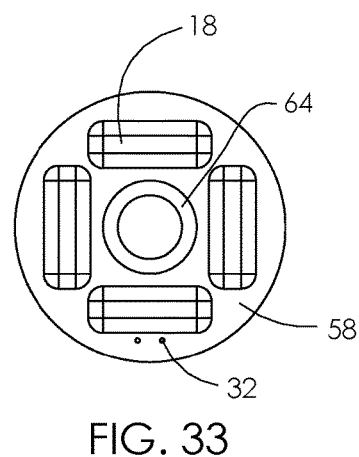
FIG. 33 is a top plan view of the PCB assembly.
Figure 34:
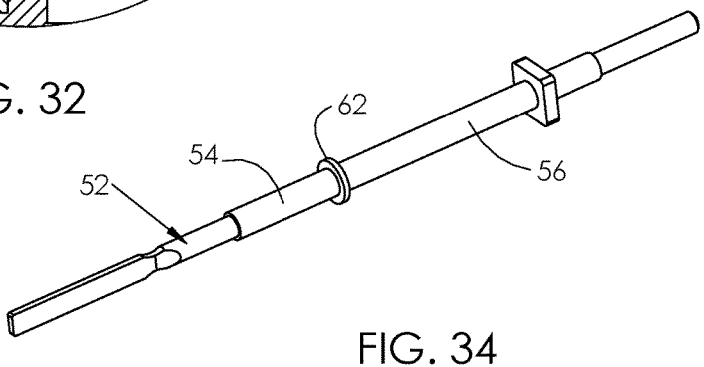
FIG. 34 is perspective view of the electrode blade.
Figure 35:
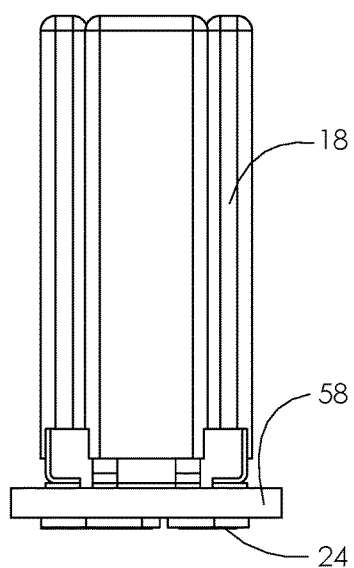
FIG. 35 is a side elevational view of the PCB assembly.
Figure 36:
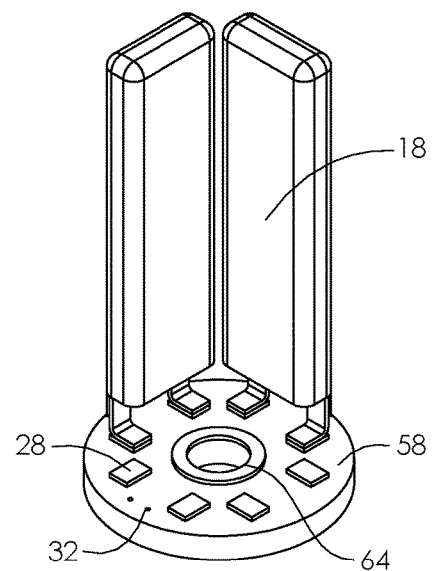
FIG. 36 is a perspective view of the PCB assembly, with two battery cells removed or better illustration.
Figure 37:
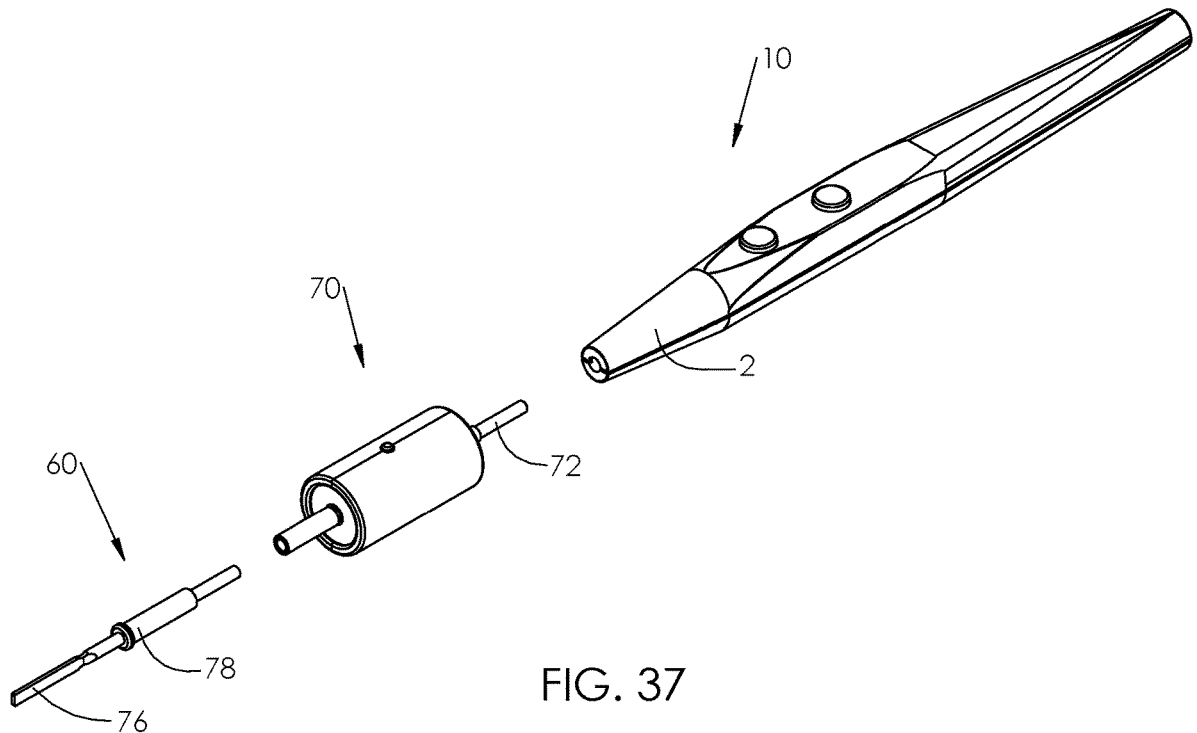
FIG. 37 is an exploded perspective view of another embodiment of the lighted blade assembly.
Figure 38:
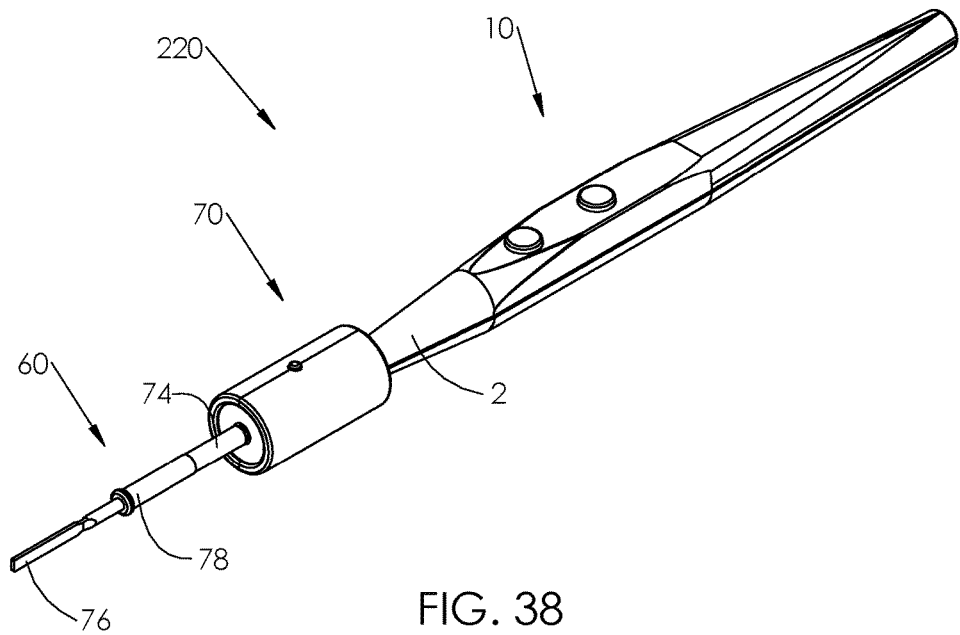
FIG. 38 is a perspective view of the lighted blade assembly of FIG. 37.
Figure 39:
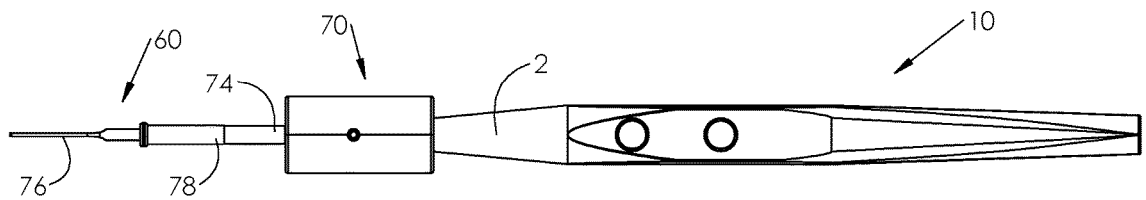
FIG. 39 and FIG. 40 shows top and side views of the lighted blade assembly of FIG. 37
Figure 40:
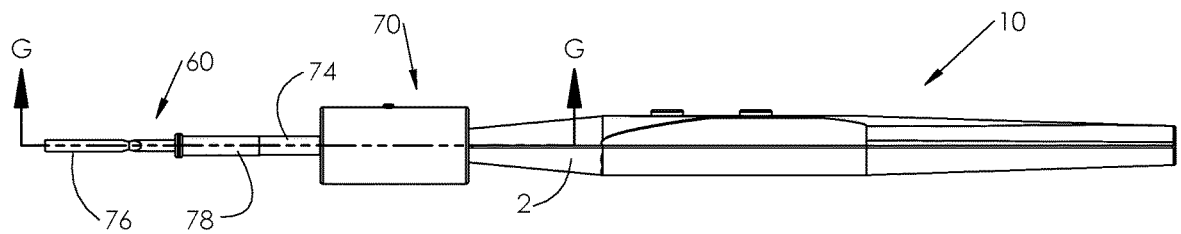

Referring to FIGS. 29 through 36, there is illustrated yet another embodiment of the lighted electrocautery blade assembly of the subject invention, which is designated generally by reference numeral 50. The lighted blade assembly 50 includes an annular PCB 58 having a plurality of circumferentially spaced apart embedded LEDs 24 that are powered by one or more rechargeable battery cells 18. The rechargeable battery cells 18 are electrically connected to an elongated conductive electrode 52 mounted in the interior cavity 15 of the housing 14, 14' of blade assembly 50. More particularly, the conductive electrode 52, has an integral annular contact boss 62 bounded by distal and proximal insulating sheaths 54 and 56, which is in face-to-face contact with a conductive ring 64 that is positioned around the central aperture of PCB 58, as best seen in FIG. 32. A switch 22 is connected to the PCB 58 by wires 26 connected at location 32 which communicate with battery contacts 28, which are best seen in FIGS. 33 and 36.

In use, RF energy passing through the electrode 52 will be converted and directed to charge the battery cells 18 on PCB 58. Thus, this embodiment of the invention relies on the battery to supply power to the LEDs 24 and does not source power directly from the RF power generator. Moreover, the RF power source is used to charge the battery cells 18, which in turn will power the LEDs 24. The rechargeable battery cell 18 (such as a Lithium Ion battery) essentially acts as the middle man and would likely be initially supplied in a partially charged state, so that the lighted blade assembly 50 could activate from first use.

Referring to FIGS. 37 through 45, there is illustrated still another embodiment of the lighted blade assembly of the subject invention, which is designated generally by reference numeral 70. Like the previously described embodiments, lighted blade assembly 70 is adapted and configured for releasable attachment to the distal end portion 2 of a handheld electrosurgical instrument 10.

Figure 44:
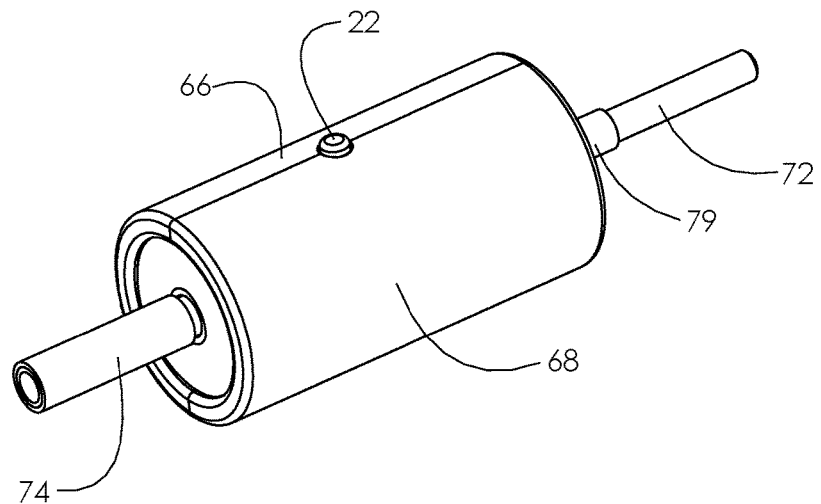
FIG. 44 is a perspective view of lighted blade assembly of FIG. 37.
Figure 45:
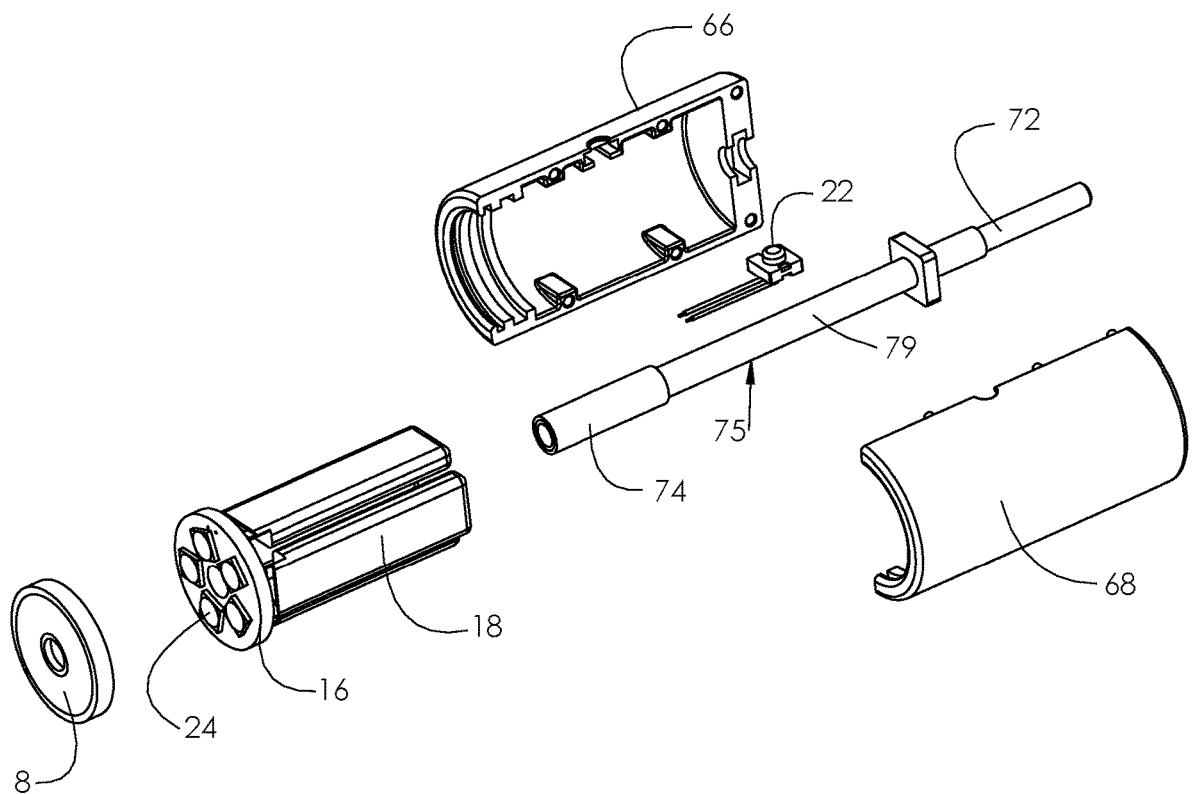
FIG. 45 is an exploded perspective view of lighted blade assembly of FIG. 37.
Figure 46:
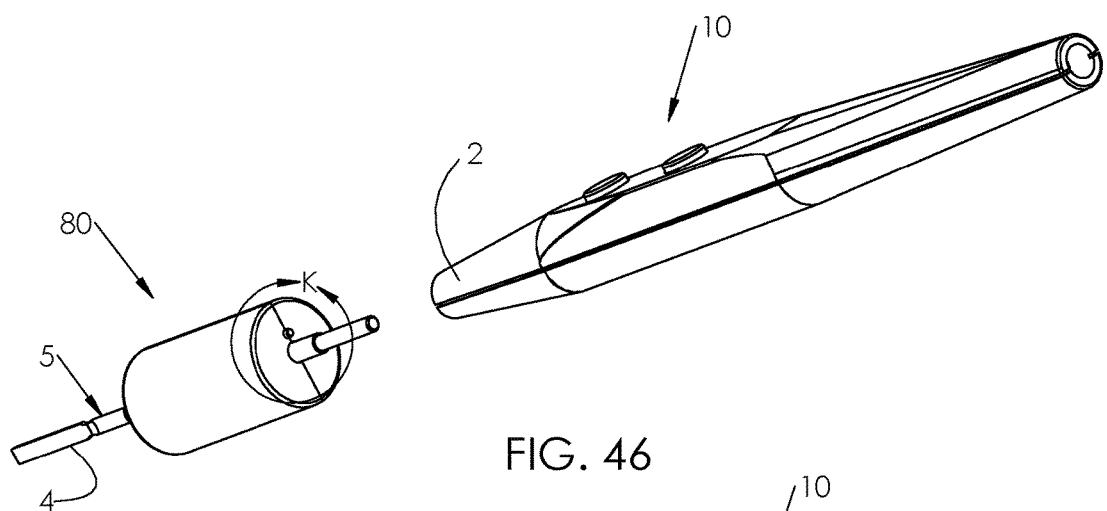
FIG. 46 shows an exploded perspective exploded view of yet another embodiment of the lighted blade assembly of the subject invention.

Referring to FIGS. 44 and 45, the lighted blade assembly 70 also includes a two-part cylindrical housing 66, 68 having an interior cavity 65 that supports an annular PCB 16 and a lens 8. The PCB 16 has a plurality of circumferentially spaced apart LEDs 24 embedded on the distal surface thereof and a plurality of battery cells 18 are operatively associated with the proximal surface of the PCB 16 for powering the LEDs 24. The PCB 16 is controlled by an actuation switch 22.

The lighted blade assembly 70 differs from the previously described embodiments of the invention in that it includes an elongated conductive electrode adapter 75 that is mounted within the interior cavity 65 of housing 66, 68. The electrode adapter 75 includes a distal reception portion 74 that extends from the distal end of the housing 66, 68 for receiving an electrocautery blade end effector 60 and a proximal connector portion 72 that extends from the proximal end of the housing 66, 68 for engagement within a reception bore 12 in the distal end 2 of surgical instrument 10. A sheath 79 is provided on the body of the elongated electrode adapter 75 between the distal reception portion 74 and the proximal connector portion 72.

Figure 41:
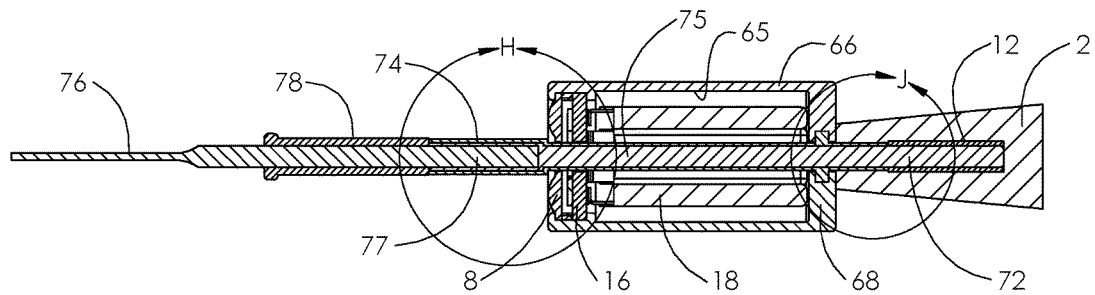
FIG. 41 is a cross-sectional view taken along line G-G of FIG. 40.
Figure 42:
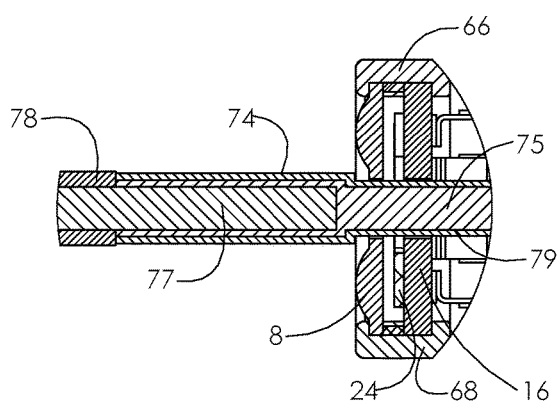
FIG. 42 is an enlarged localized view of area H taken from FIG. 41.
Figure 43:
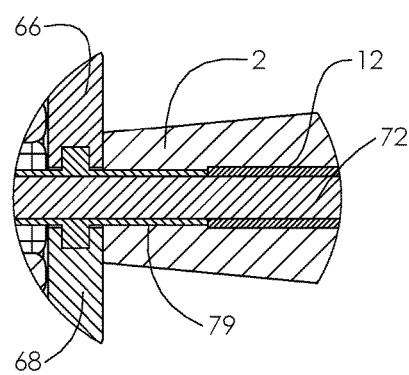
FIG. 43 is an enlarged localized view of area J taken from FIG. 41.

Referring to FIG. 41 through 43, the electrocautery blade end effector 60 has a distal blade section 76 and a proximal connector section 77, with a portion of the proximal connector section having an insulating sheath 78. When the proximal connector section 77 is inserted into the distal reception portion 74 of electrode adapter 75, the proximal end of the connector section 77 is in abutting electrical contact with the distal end of the conductive electrode adapter 75, so that RF energy is delivered from the surgical instrument 10, through the body of the electrode adapter 75 to the end effector 60.

By providing the lighted blade assembly 70 with an electrode adaptor 75, the user has the freedom to swap out electrode tips during a procedure. Moreover, during surgery, it is possible that a surgeon would want to begin operating with a blade electrode, switch to a ball electrode to cauterize certain anatomy, then switch to a loop electrode to remove diseased tissue, and then go back to the blade electrode to finish the procedure. The electrode adaptor 75 allows for that freedom.

Figure 47:
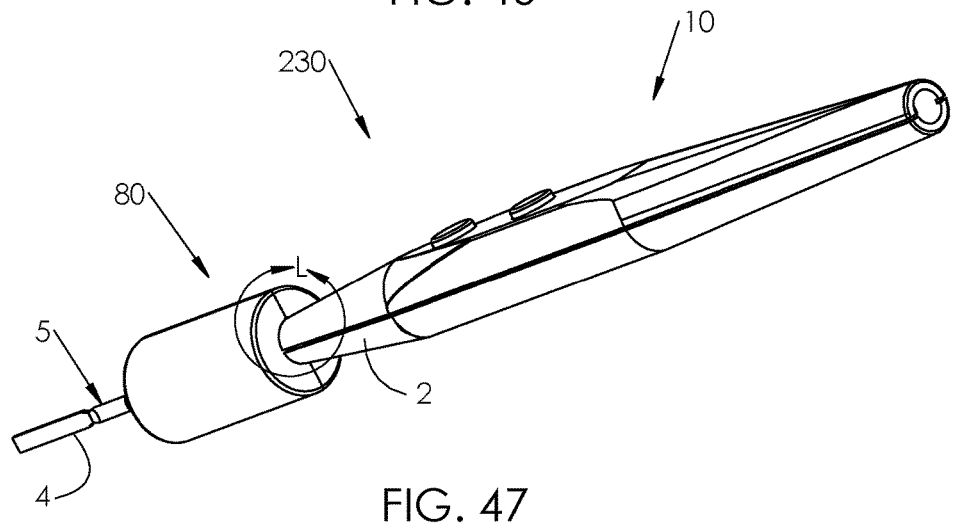
FIG. 47 is a perspective view of the lighted blade assembly of FIG. 46 attached to a surgical instrument.
Figure 48:
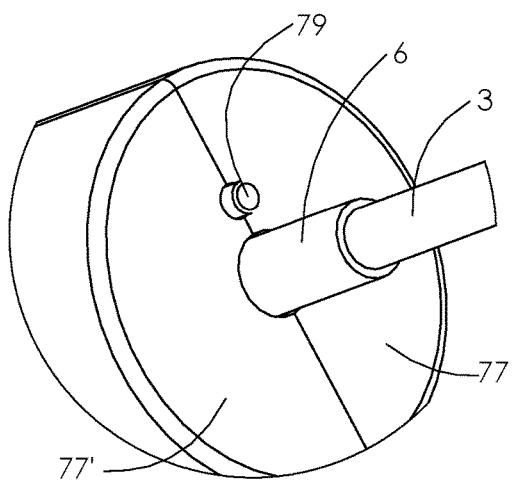
FIG. 48 is an enlarged localized view of area K taken from FIG. 46.
Figure 49:
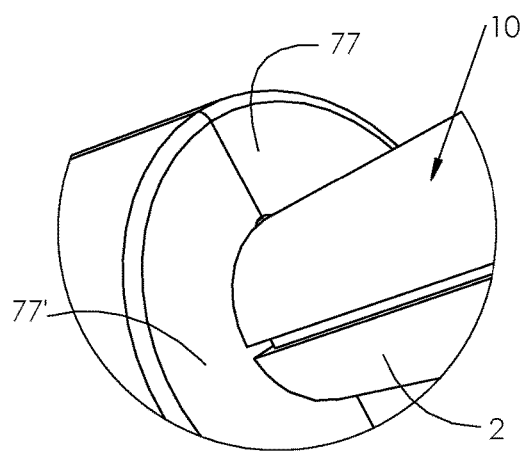
FIG. 49 is an enlarged localized view of area L taken from FIG. 47.
Figure 50:
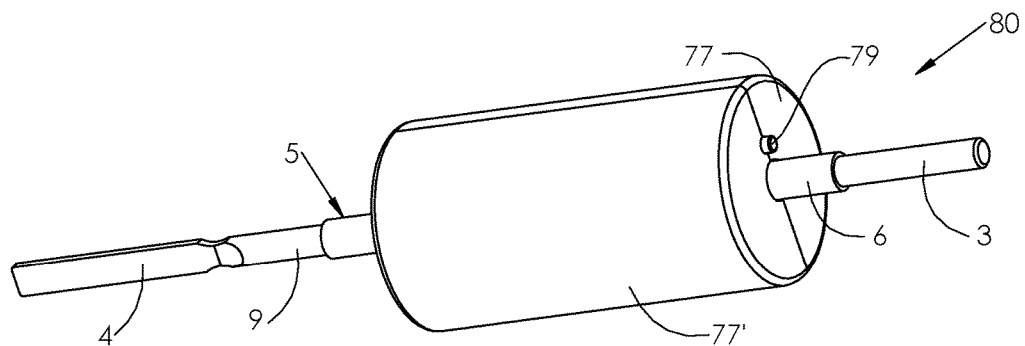
FIG. 50 is a perspective view of lighted blade assembly of FIG. 46.
Figure 51:
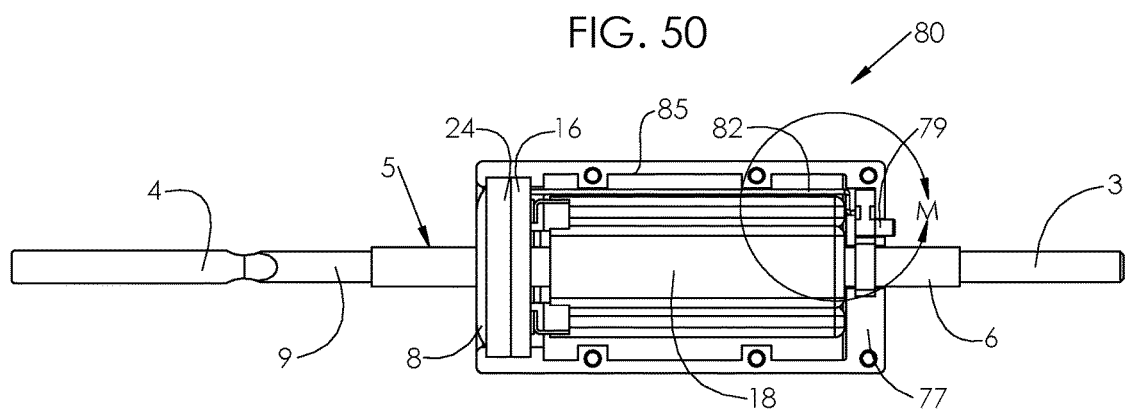
FIG. 51 is a perspective view of light blade assembly of FIG. 46 with a portion of the body removed for better illustration of the interior.
Figure 52:
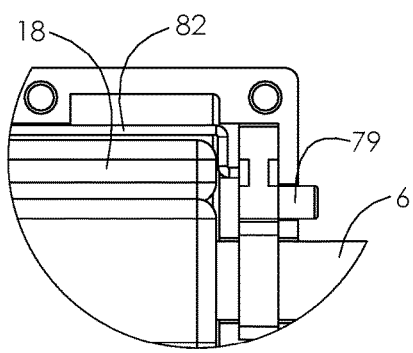
FIG. 52 is an enlarged localized view of area M of FIG. 51.
Figure 53:
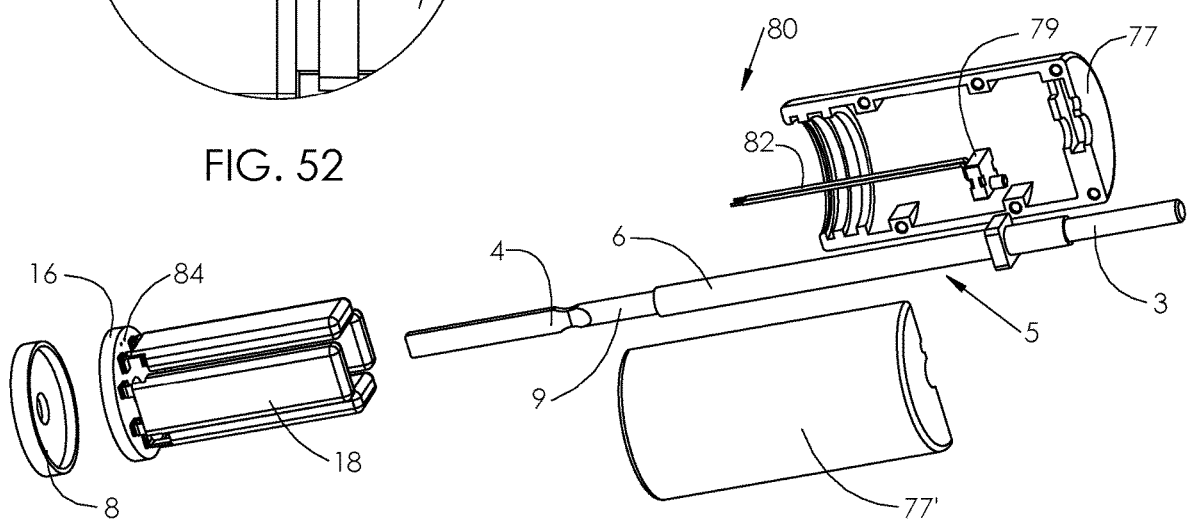
FIG. 53 is an exploded perspective view of lighted blade assembly of FIG. 46.
Figure 54:
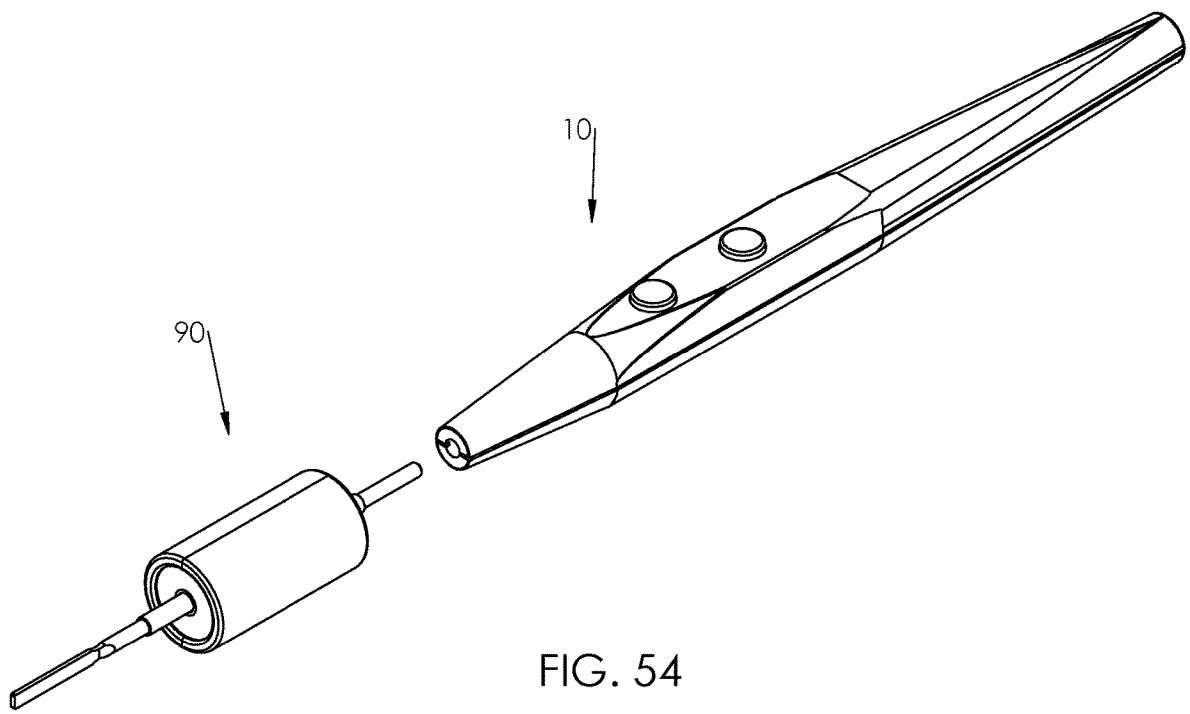
FIG. 54 is a perspective view of still another embodiment of the lighted blade assembly of the subject invention separated from a surgical instrument.
Figure 55:
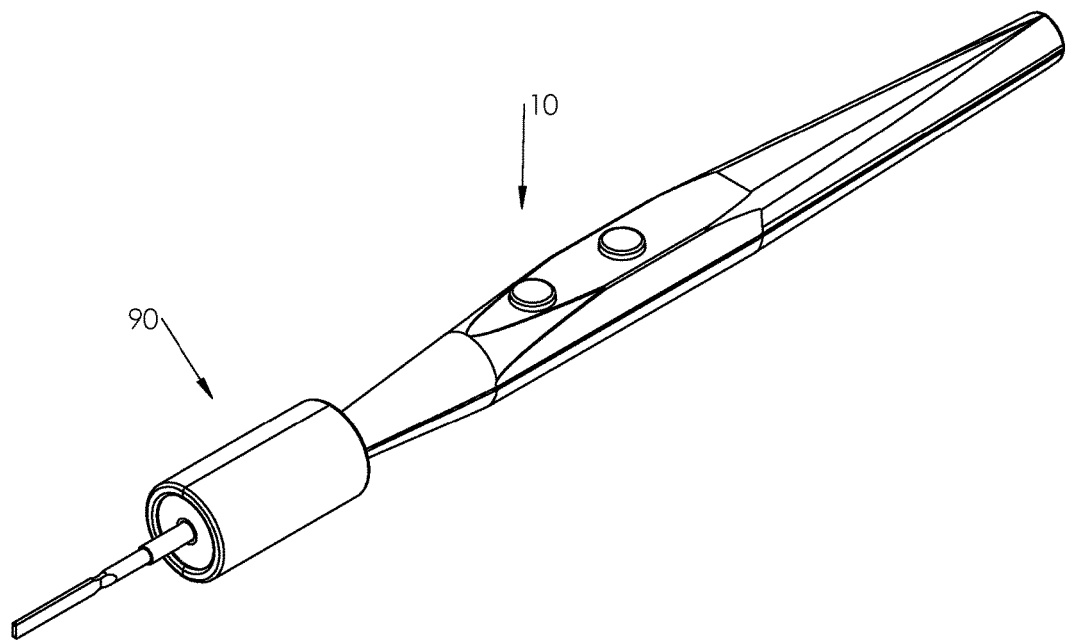
FIG. 55 is a perspective view of the lighted blade assembly of FIG. 54 attached to a surgical instrument.
Figure 63:
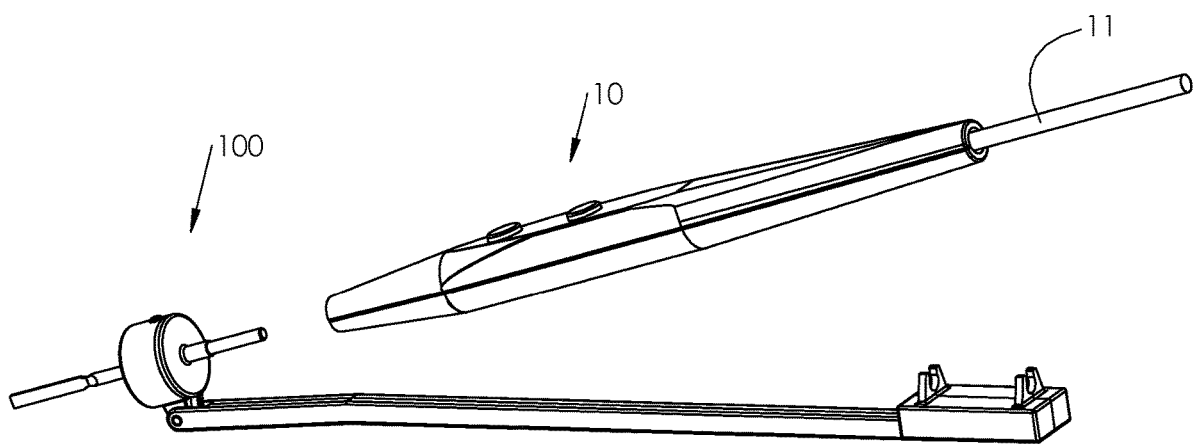
FIG. 63 is a perspective view of yet another embodiment of the lighted blade assembly of the subject invention detached from a surgical instrument.

Referring now to FIGS. 46 through 53, there is illustrated another embodiment of the lighted blade assembly of the subject invention, which is designated generally by reference numeral 80. This embodiment of the lighted blade assembly is substantially similar to the embodiment designated by reference numeral 20 shown in FIG. 8, but in this embodiment the energy cells 18 associated with PCB 16 are controlled by a push-button actuation switch 79 that is operatively associated with a proximal surface of the elongated housing 77, 77' so as to interact with an end surface of the distal portion 2 of the electrosurgical instrument 10, when the lighted electrocautery blade assembly 80 is attached thereto, as illustrated in FIGS. 47 and 49.

More particularly, the actuation switch 79 is electrically connected to the PCB 16 by internal electrical connections 82 that extend through the interior cavity 85 of housing 77, 77' so that the LEDs 24 on PCB 16 will automatically illuminate when the switch 79 is depressed against the end surface of the distal portion 2 of surgical instrument 10 upon insertion of the proximal connector 3 of electrode 5 is inserted into the distal end 2 of instrument 10.

Referring to FIGS. 54 through 62, there is illustrated yet another embodiment of a lighted blade assembly of the subject invention, which is designated generally by reference numeral 90. This embodiment of the lighted blade assembly is substantially similar to the previous embodiment of the invention illustrated in FIG. 50, except that it does not include a push-button actuation switch for selectively controlling the delivery of power to the LEDs 24 embedded in the distal surface of PCB 16. Instead, the lighted blade assembly 90 includes an automatic light activation switch in the form of a sensor 96 that is located within the interior cavity 85 of the blade housing 86, 86'. The sensor 96 could be a Hall-effect sensor, for example.

More particularly, the sensor 96 is located on the proximal surface of the PCB 16 behind lens 8 and is adapted to detect activation of the electrocautery instrument 10 and the flow of power through the elongated electrode body 88. In use, when RF energy flows through the electrode body 88 due to activation of the surgical instrument 10, the sensor 96 will detect that electricity and cause power to be delivered from the battery cells 18 to the LEDs 24 on PCB 16. Alternatively, this is accomplished by connecting the sensor 96 to a conductive annular boss 94 formed on the electrode body 88 by way of a contact prong 102, best seen in FIG. 61. The annular boss 94 on electrode body 88 is located between the proximal and distal insulating sheaths 92 and 98. The sensor 96 will detect electricity flow and cause power to be delivered from the battery cells 18 to the LEDs 24 on PCB 16.

It is envisioned that the sensor 96 could be coupled with a logic chip (not shown) that would enable the LEDs to stay illuminated for a predetermined period of time following their initial activation. Surgeons typically cut or cauterize tissue for short periods of time (i.e., short bursts of ~1 second with breaks in between). As such, the logic chip would keep the LEDs illuminated for a period of e.g., 30 seconds following an activation, and then turn the LEDs off if the instrument is not in use, thus conserving battery power.

Figure 76:
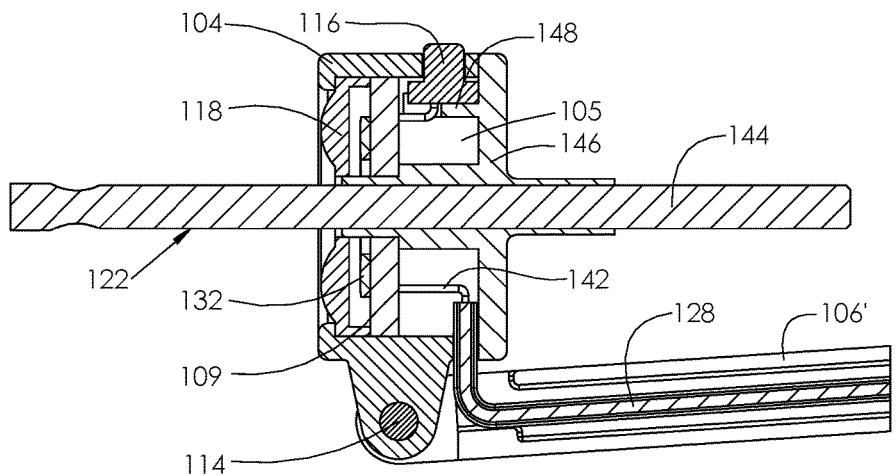
FIG. 76 is an enlarged cross-sectional view taken along line S-S of FIG. 71.

Referring now to FIGS. 63 through 79, there is illustrated still another embodiment of the lighted blade assembly of the subject invention, which is designated generally by reference numeral 100. The lighted blade assembly 100 includes a cylindrical housing 104 having an interior cavity 105 that supports an annular PCB 109 with a plurality of LEDs 132 embedded on the distal surface thereof, and a lens 118 located in front of the LEDs 132, as best seen in FIG. 76. An elongated electrode body 122 is also supported within the housing 104, and it includes a distal blade portion 121 and a proximal connector portion 144.

Figure 77:
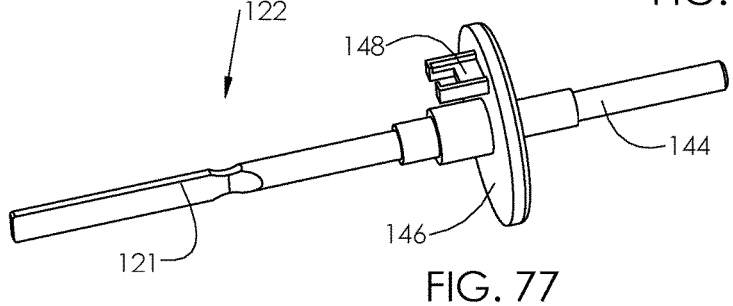
FIG. 77 is a perspective view of the electrode of the lighted blade assembly.
Figure 78:
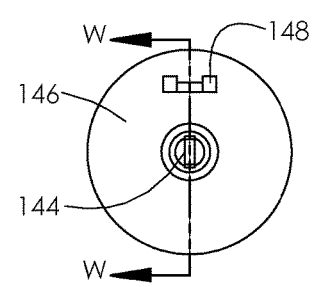
FIG. 78 is a front elevational view of the electrode in FIG. 77.
Figure 79:
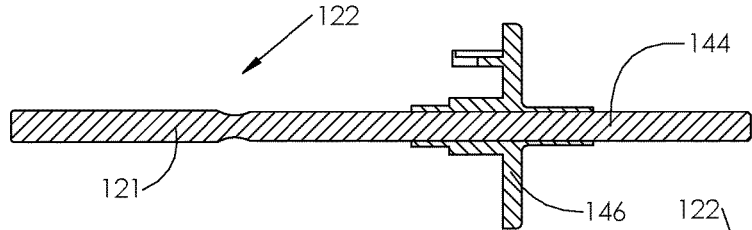
FIG. 79 is a cross-sectional view taken along line W-W of FIG. 78.

As best seen in FIG. 76 through 78, an isolative end cap 146 is supported on the electrode body 122 for enclosing the interior cavity of housing 104 from the proximal end thereof. A push button on-off switch 116 is operatively associated with the outer periphery of the housing 104 and it is supported on a distally extending shelf 148 formed on an interior surface of end cap 146. The switch 116 is electrically connected to the PCB 109 for selectively controlling power delivery to the LEDs 132 embedded thereon.

Figure 66:
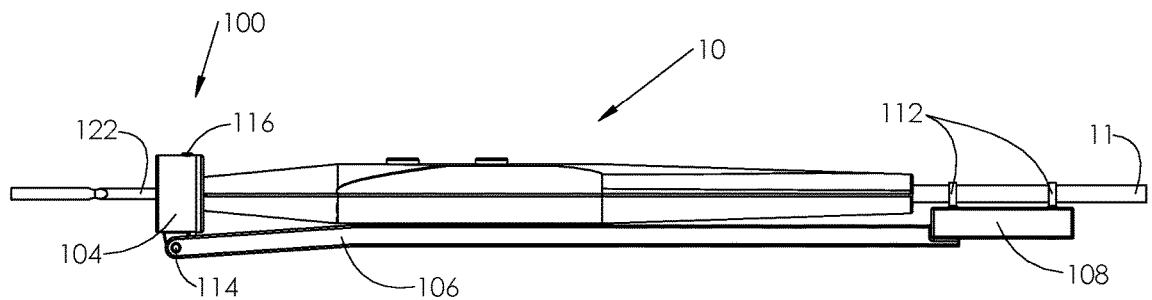
FIG. 66 is a side elevational view of the lighted blade assembly of FIG. 63 attached to a surgical instrument as shown in FIG. 65.
Figure 67:
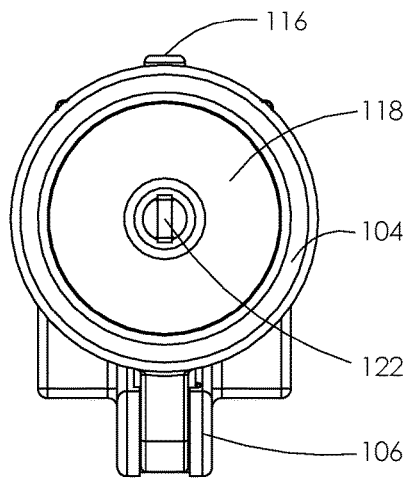
FIGS. 67 and 68 are front and back elevational views, respectively, of the lighted blade assembly and surgical instrument shown in FIG. 65.
Figure 68:
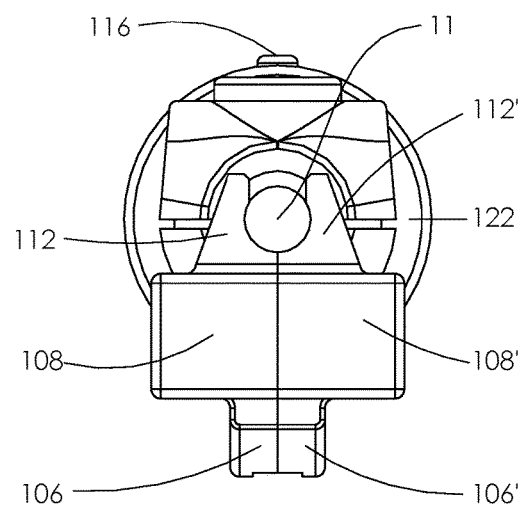
Figure 69:
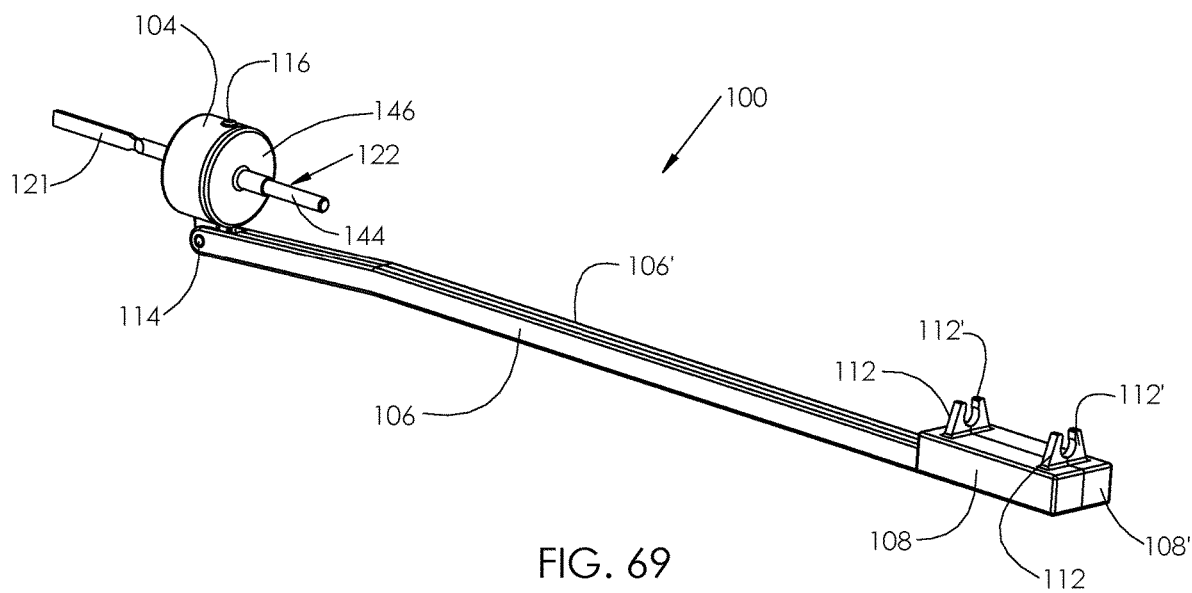
FIG. 69 is a perspective view of the lighted blade assembly shown in FIG. 65.
Figure 70:
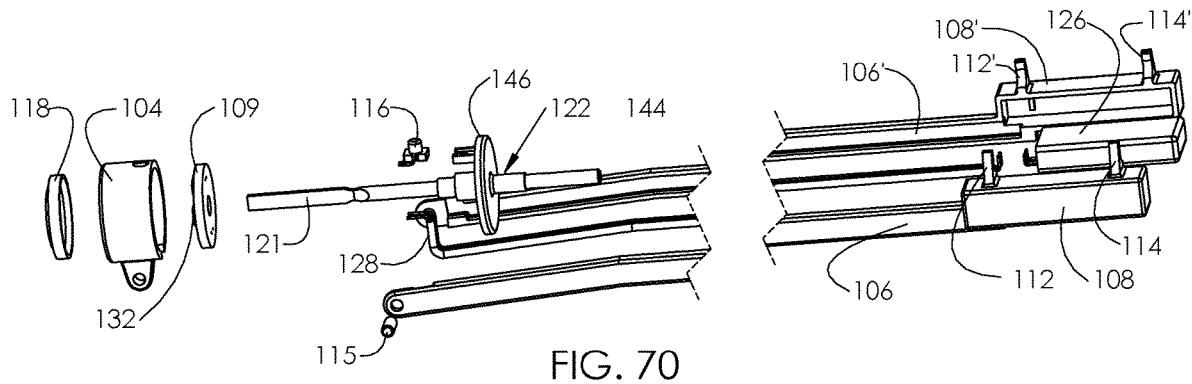
FIG. 70 is an exploded perspective view of the lighted blade assembly in FIG. 65.
Figure 71:
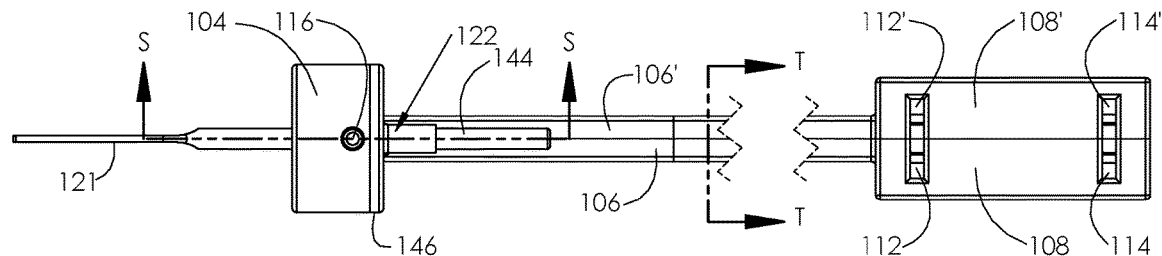
FIG. 71 is a top plane view of the lighted blade assembly shown in FIG. 65.
Figures 73, 74, 75:
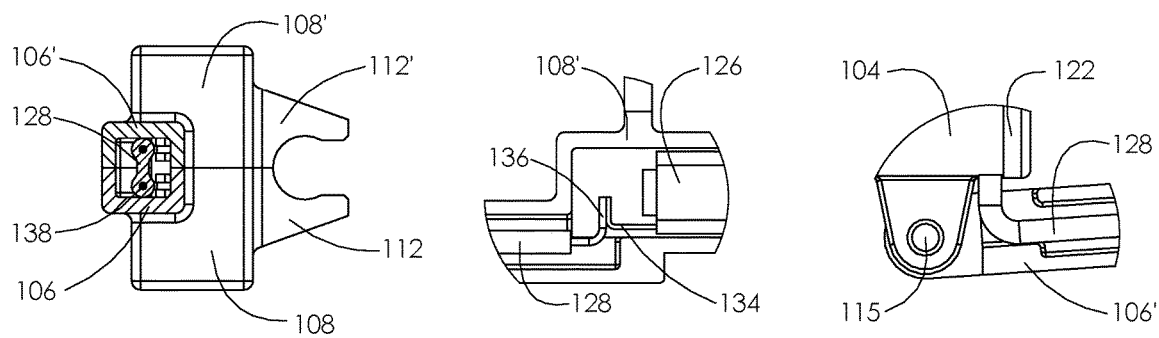
FIG. 73 is a cross-sectional view taken along line T-T of FIG. 71.
FIG. 74 is an enlarged localized view of area V taken from FIG. 72.
FIG. 75 is an enlarged localized view of area U taken from FIG. 72.

The PCB 109 is electrically connected to a remote battery cell 126 by way of an elongated electrical cable 128. More particularly, as shown in FIG. 76, the elongated cable 128 has a distal terminal 142 for connection to the proximal surface of PCB 109 and a proximal terminal 136 for connection to a terminal 134 of battery cell 126, as best seen in FIG. 74. Battery cell 126 is enclosed within a two-part rectangular housing 108, 108'. A pair of U-shaped clasps 112, 112' and 114, 114' are provided on an upper surface of the battery housing 108, 108' to releasably secure the battery housing 108, 108' to the RF power cable 11 associated with the electrosurgical instrument 10, as best seen in FIGS. 66 and 68.

Figure 72:
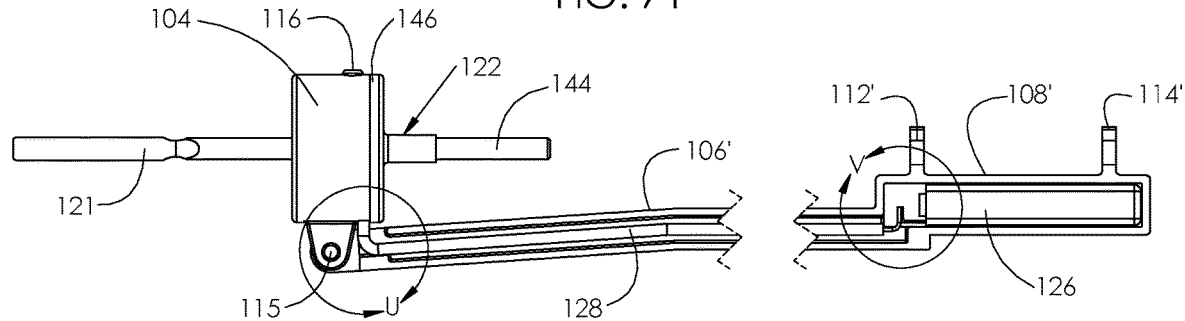
FIG. 72 is a side elevational view of the of the lighted blade assembly shown in FIG. 65, with the side cover removed for ease of illustration.

The lighted blade assembly 100 further includes an elongated two-part link body 106, 106' for operatively connecting the blade housing 104 to the battery housing 108, 108'. More particularly, the link body 106, 106' is integrally formed with the two-part housing 108, 108' and the distal end thereof is hingedly connected to the blade housing 104 by way of a transverse pivot pin 115, best seen in FIG. 75. As best seen in FIGS. 72 and 73, the elongated electrical cable 128 extends through and is advantageously supported with the interior of link body 106, 106'. Those skilled in the art will readily appreciate locating the battery remote from the line of sight of the surgeon reduces the bulk of the device at the distal use area.

Figure 80:
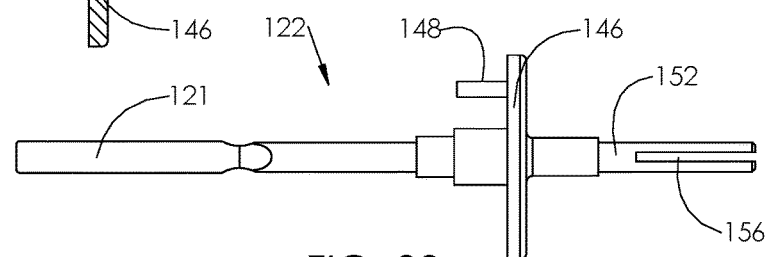
FIG. 80 is a side elevational view of an electrode, with a slotted proximal portion for adjusting to different sizes of connectors of surgical instruments.
Figure 81:
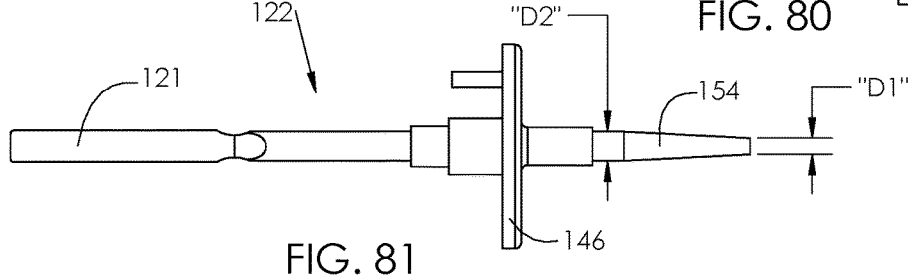
FIG. 81 is a side elevational view of an electrode, with a tapered proximal portion for adjusting to different sizes of connectors of surgical instruments.
Figure 82:
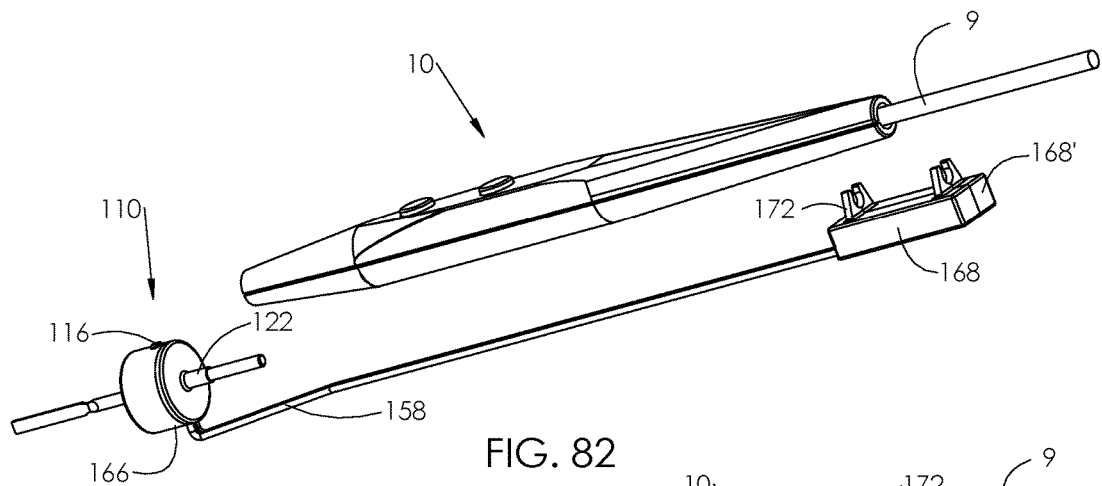
FIG. 82 is a perspective view of still another embodiment of the lighted blade assembly of the subject invention detached from a surgical instrument.

It is envisioned that the proximal connector portion 144 of the elongated electrode 122 may vary to facilitate the attachment of the lighted blade assembly to different sized or types of electrosurgical instruments that are currently or may become available in the marketplace. For example, the electrode 122 can have a proximal connector portion 152 with a slot 156 that creates a compressible bifurcated connector portion as illustrated in FIG. 80, or the electrode 122 can have a proximal connector portion 154 that conically tapers from a distal diameter D2 to a proximal diameter D1, as illustrated in FIG. 81.

Referring now to FIGS. 82 through 87, there is illustrate yet another embodiment of the lighted blade assembly of the subject invention, which is designated generally by reference numeral 110. This embodiment of the lighted blade assembly is substantially similar to the lighted blade assembly 100 shown in FIG. 69, except that it does not include a hinged link body between the cylindrical blade housing 166 and the remote battery housing 168, 168' that is attached to the RF power cord 9 of surgical instrument 10. Instead, the elongated electrical power cord 158 extends freely between the blade housing 166 and the battery housing 168, 168'.

Figure 64:
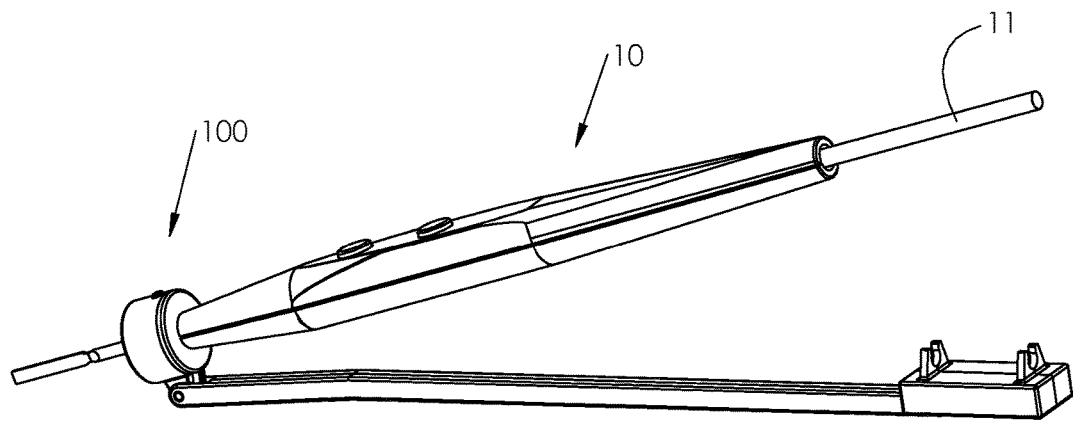
FIG. 64 is a perspective view of the lighted blade assembly of FIG. 63 with the distal portion of the assembly attached to the distal end of the surgical instrument.
Figure 65:
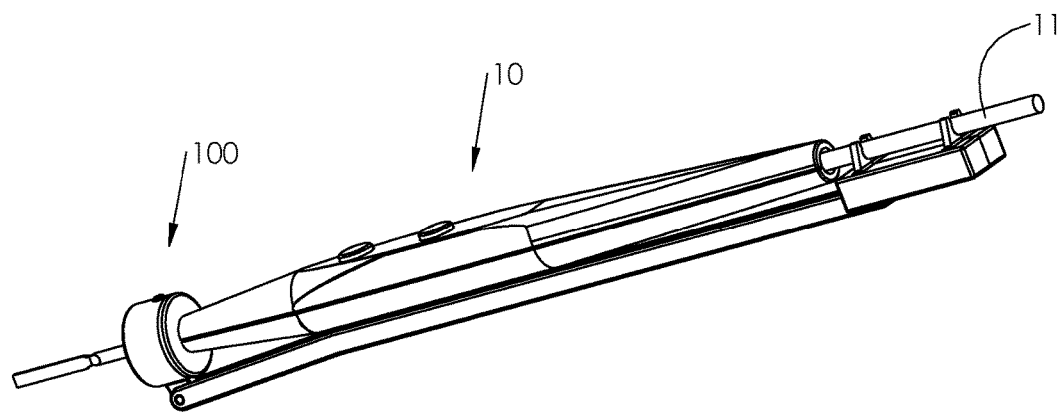
FIG. 65 is a perspective view of the lighted blade assembly of FIG. 63 fully attached to a surgical instrument and the power cable associated therewith.
Figure 83:
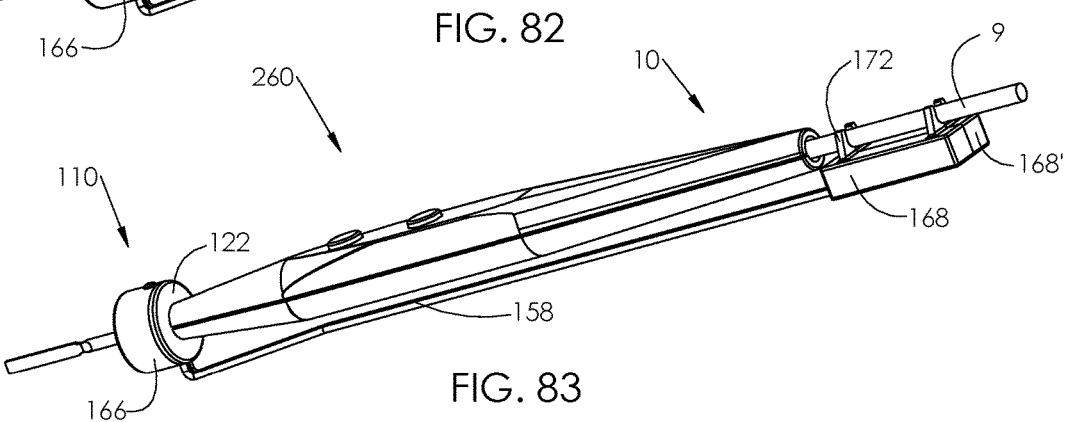
FIG. 83 is a perspective view as in FIG. 82, with the lighted blade assembly attached to the surgical instrument.
Figure 84:
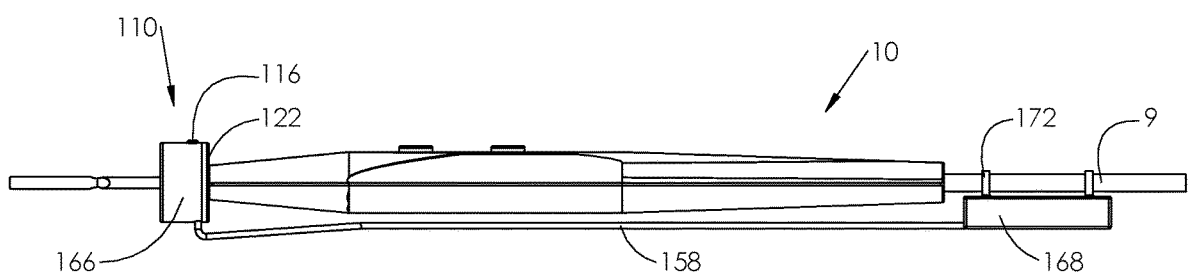
FIG. 84 is a side elevational view of the lighted blade assembly and surgical instrument as shown in FIG. 83.
Figure 85:
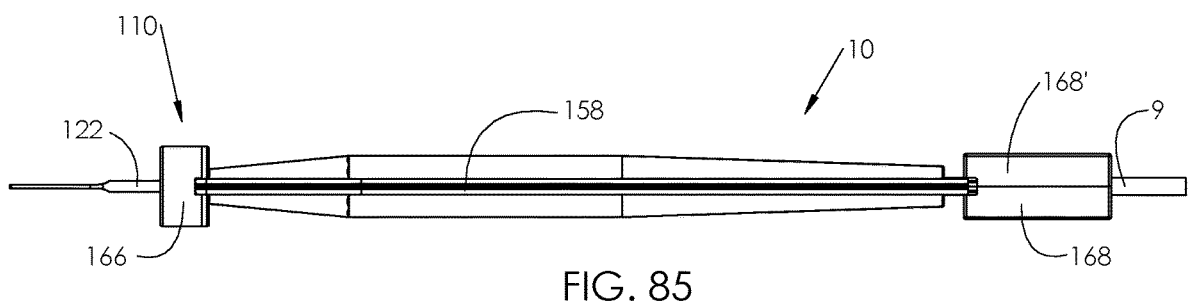
FIG. 85 is a bottom plan view of the lighted blade assembly and surgical instrument as shown in FIG. 83.
Figure 86:
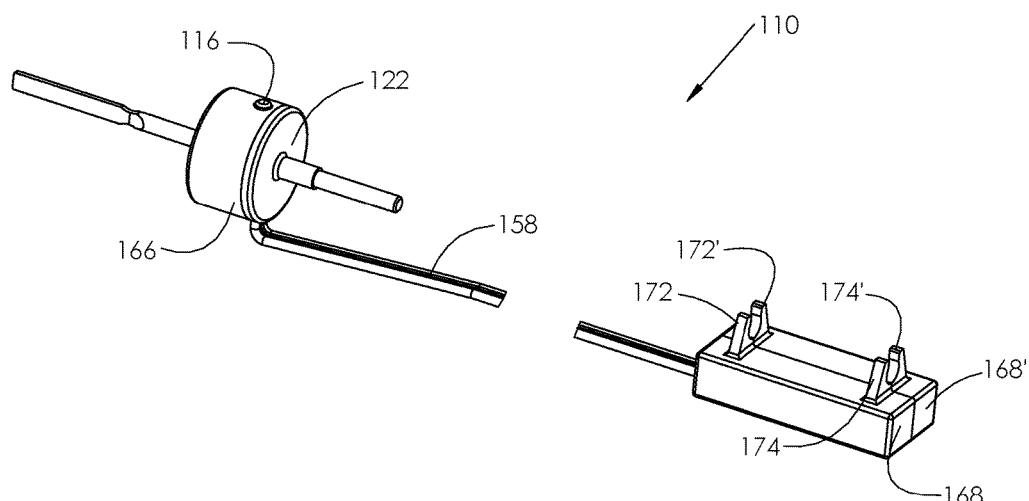
FIG. 86 is a perspective view of the lighted blade assembly shown in FIG. 82.
Figure 87:
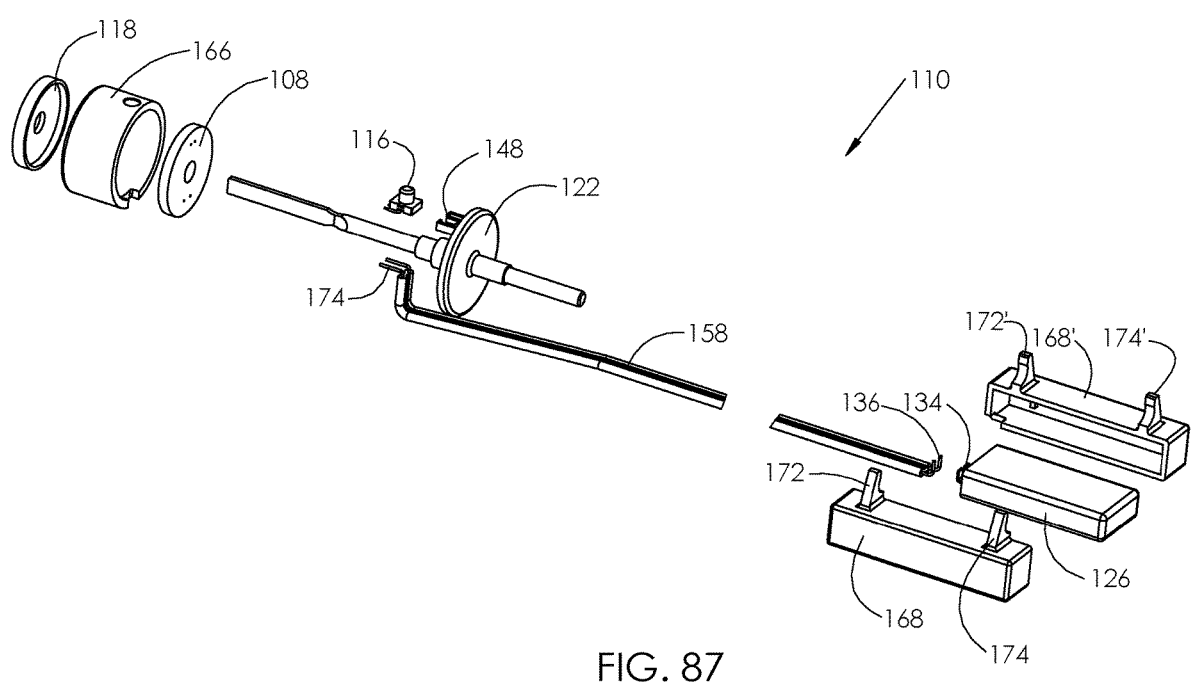
FIG. 87 is an exploded perspective view of the lighted blade assembly of FIG. 82.
Figure 88:
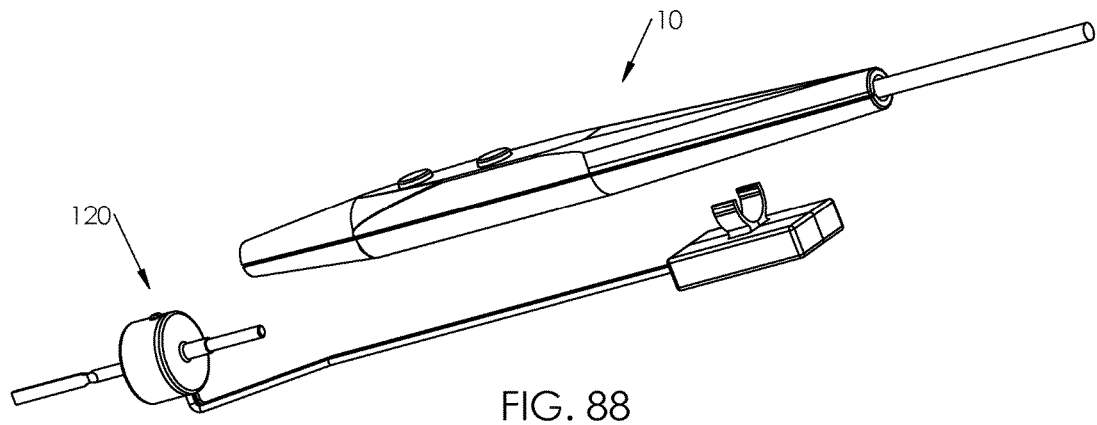
FIG. 88 is a perspective view of yet another lighted blade assembly separated from a surgical instrument.

More particularly, as best seen in FIGS. 86 and 87, the elongated electrical power cord 158 has a distal terminal 174 for connection to the annular PCB 108 supported within the housing 166 behind lens 118 and a proximal terminal 136 for connection with a terminal 134 of battery cell 126. As in the previous embodiment of the invention, a pair of U-shaped clasps 172, 172' and 174, 174' are provided on an upper surface of the battery housing 168, 168' to releasably secure the battery housing 168, 168' to the RF power cable 9 associated with the electrosurgical instrument 10, as best seen in FIGS. 83 and 64.

Figure 89:
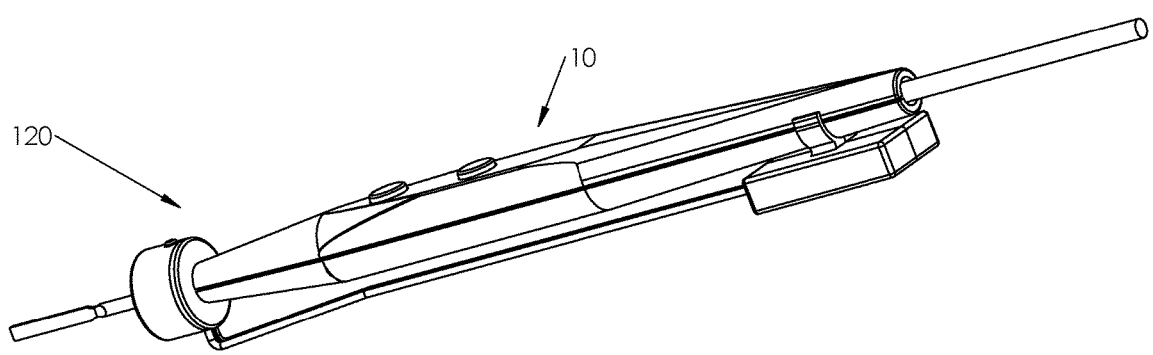
FIG. 89 is a perspective view of the lighted blade assembly show in FIG. 88 attached to the surgical instrument.
Figure 90:
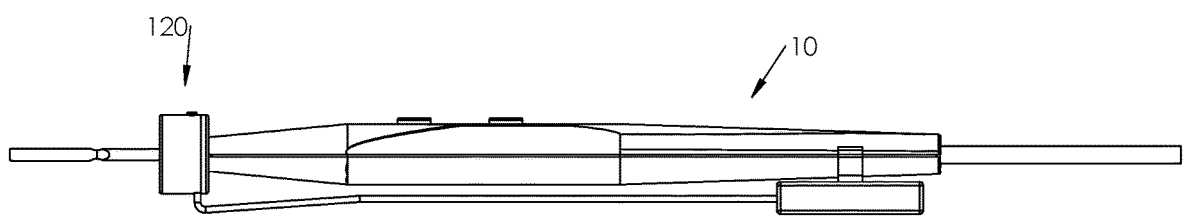
FIG. 90 is a side elevational view of the lighted blade assembly and surgical instrument as shown in FIG. 89.
Figure 91:
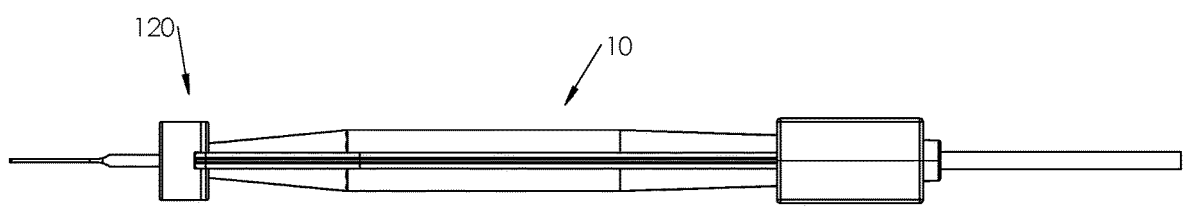
FIG. 91 is a bottom plan view of the lighted blade assembly and surgical instrument as shown in FIG. 89.
Figure 96:
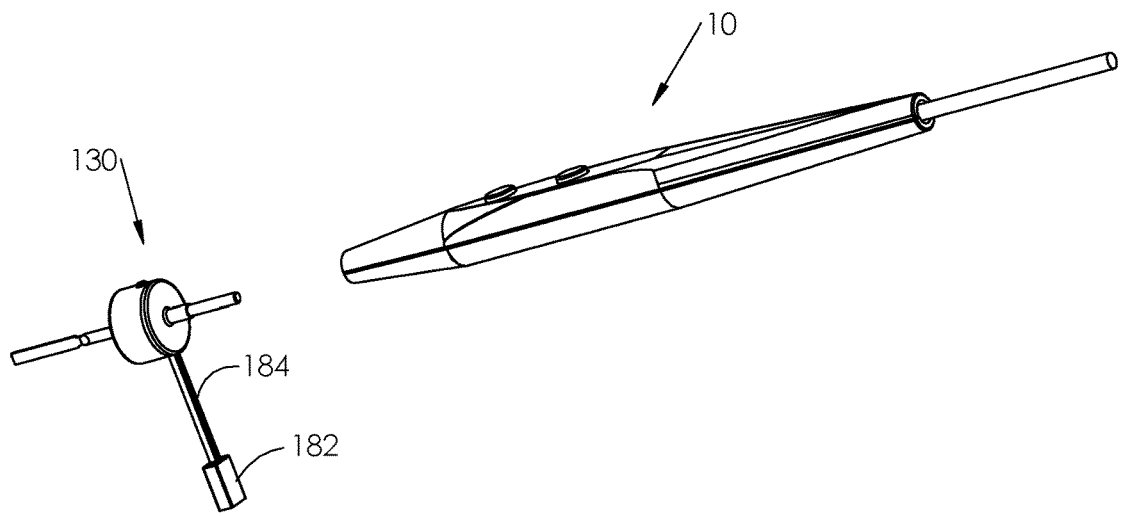
FIG. 96 is a perspective view of another lighted blade assembly with a connector for engaging with an external battery pack.
Figure 97:
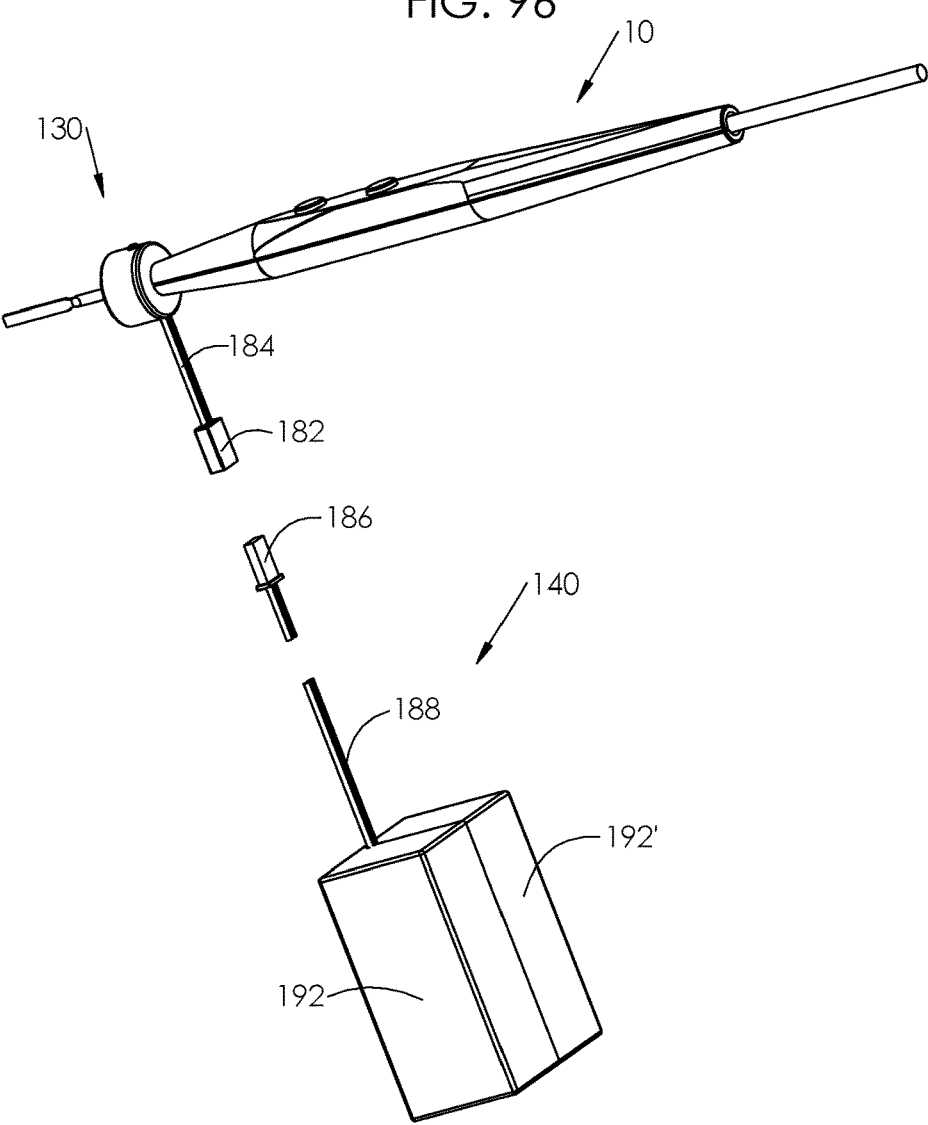
FIG. 97 is a perspective view of the lighted blade assembly of FIG. 96 attached to the surgical instrument.
Figure 98:
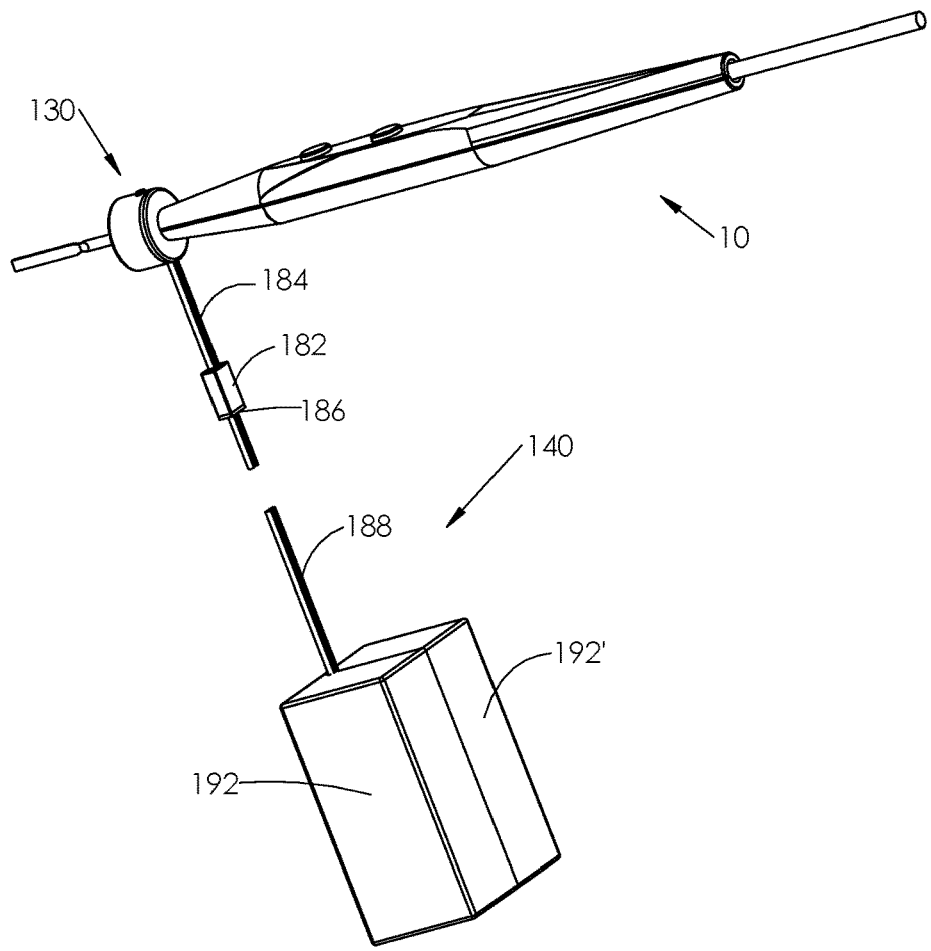
FIG. 98 is a perspective view of the lighted blade assembly, and battery pack connected to one another.
Figure 99:
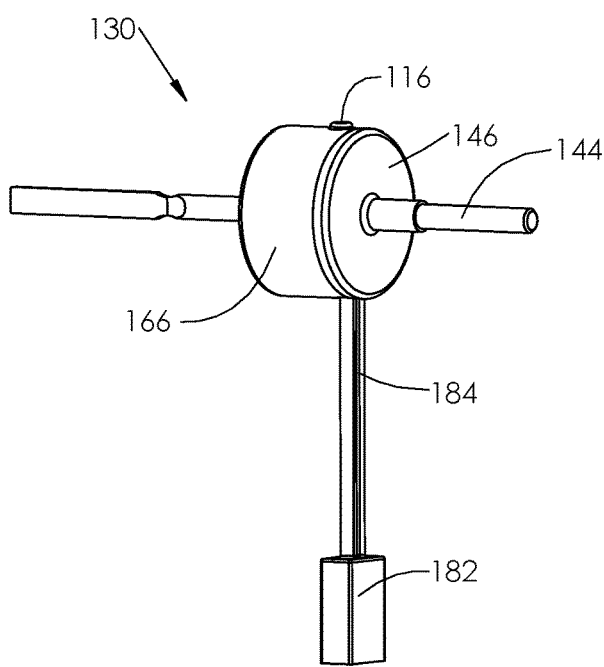
FIG. 99 is a perspective view of the lighted blade assembly of FIG. 96.
Figure 100:
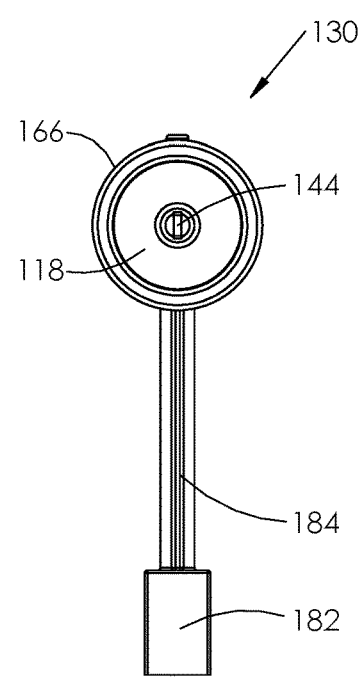
FIG. 100 is a front elevational view of the lighted blade assembly of FIG. 96.

Turning now to FIGS. 88 through 95, there is illustrated another embodiment of the lighted blade assembly of the subject invention, which is designated generally by reference numeral 120. This embodiment of the lighted blade assembly is substantially identical to the lighted blade assembly 110 shown in FIG. 86, except that it includes a remote battery housing 176, 176' with a single engagement clasp 178, 178' that is adapted and configured to releasably secure the battery housing 176, 176' to the proximal end portion of the surgical instrument 10, as opposed to the RF power cable associated therewith, as best seen in FIGS. 89 and 93.

Referring to FIGS. 96 through 103, the subject invention is also directed to a lighted electrocautery blade assembly 130 for attachment to a handheld electrosurgical instrument 10 which is powered by a remote battery pack 140. The blade assembly 130 includes a cylindrical housing 166 having a proximal end plate 146 that encloses an interior cavity supporting an annular lens 118 and a PCB 108 having a plurality of embedded LEDs on a distal surface thereof for illuminating a surgical site.

An elongated electrode body 114 is operatively supported within the housing 166 by the proximal end plate 146. A cable 184 extends from the PCB 108, through the wall of the housing 166 and terminates at a coupling box 182. The coupling box 182 is adapted and configured to mate with a connector tab 186 at the end of a cable 188 extending from a terminal 196 on an external battery 194 that is contained within a two-part battery housing 192, 192' of remote battery pack 140. A switch 116 associated with the housing 166 of blade assembly 130 controls the power from the battery pack 140 to the PCB 108, for selectively illuminating the LEDs associated therewith.

It is envisioned that the remote battery pack 140 could be located on the surgical table, on the floor, or even outside the sterile field. The cable length allows the battery pack 140 to be out of the way, without requiring the user to lift the weight of the battery, which would allow it to be much bigger and provide more power to the LEDs. The connector tab 186 also allows for the battery pack 140 to be replaced (and recharged) if needed to extend use time of the lighting device.

Referring to FIGS. 104 through 109, the subject invention is also directed to a lighted electrocautery blade assembly 140 for attachment to a handheld electrosurgical instrument 10, which includes a two-part cylindrical housing 202, 202' having an interior cavity 205 supporting a lens 204, a PCB 218 having a plurality of embedded LEDs 224 on a distal surface thereof and a plurality of battery cells 212 associated with a proximal surface thereof for powering the LEDs 224. A push-button actuation switch 116 is associated with the housing 202, 202' for selectively controlling the LEDs 224 by way of internal wires 114 that are connected to PCB 218.

Figure 105:
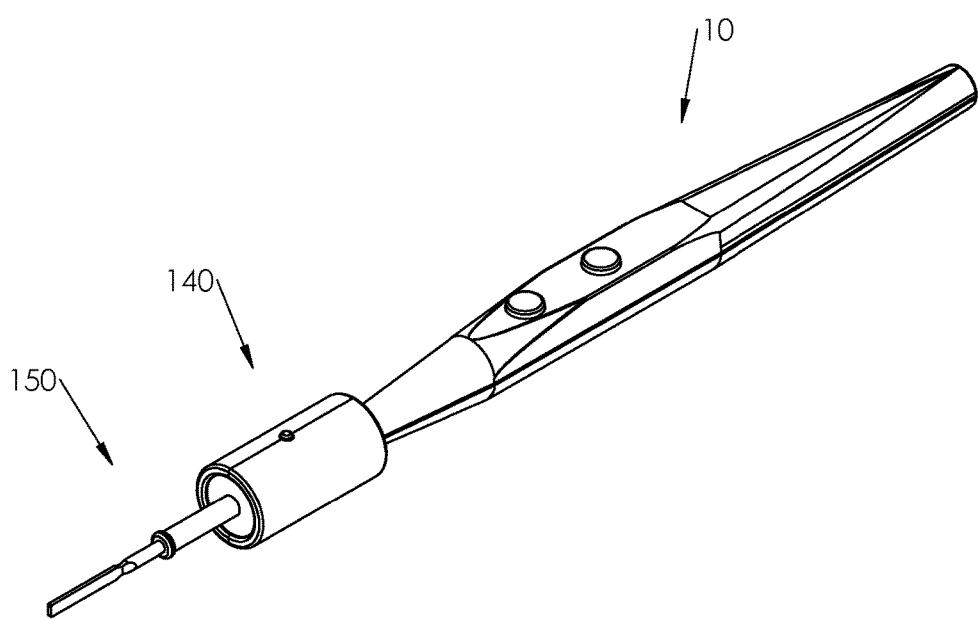
FIG. 105 is a perspective view of the lighted blade assembly of FIG. 104 attached to the distal end portion of the surgical instrument.
Figure 106:
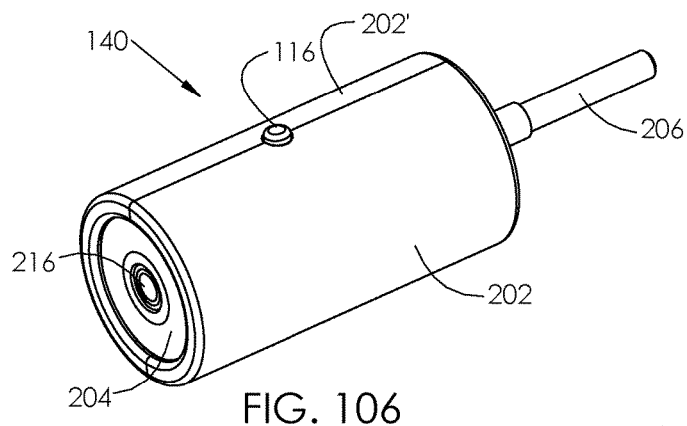
FIG. 106 is a perspective view of the lighted blade assembly of FIG. 104 with the electrode blade removed therefrom.
Figure 107:
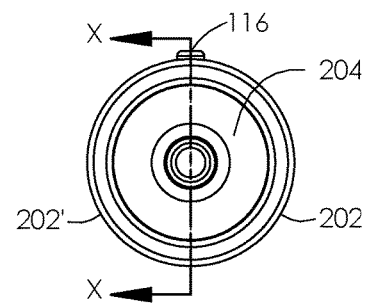
FIG. 107 is a front elevational view of the lighted blade assembly of FIG. 106.
Figure 108:
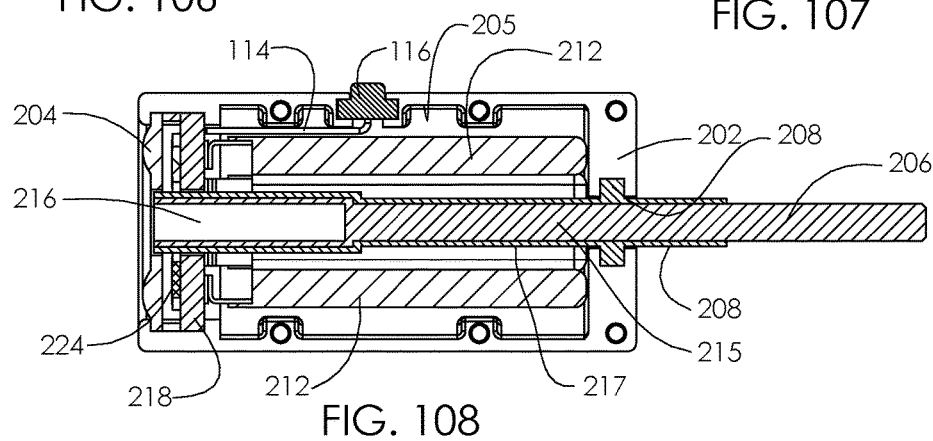
FIG. 108 is a cross-sectional view taken along line X-X of FIG. 107.
Figure 109:
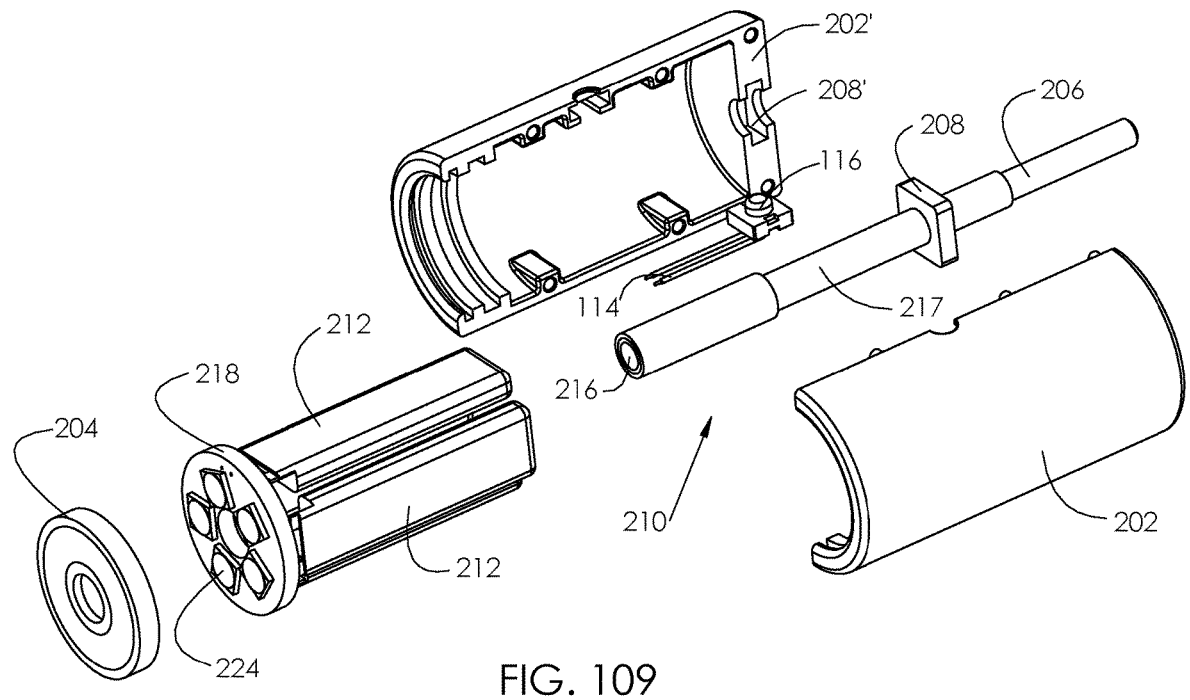
FIG. 109 is an exploded perspective view of the lighted blade assembly of FIG. 106.
Figure 110:
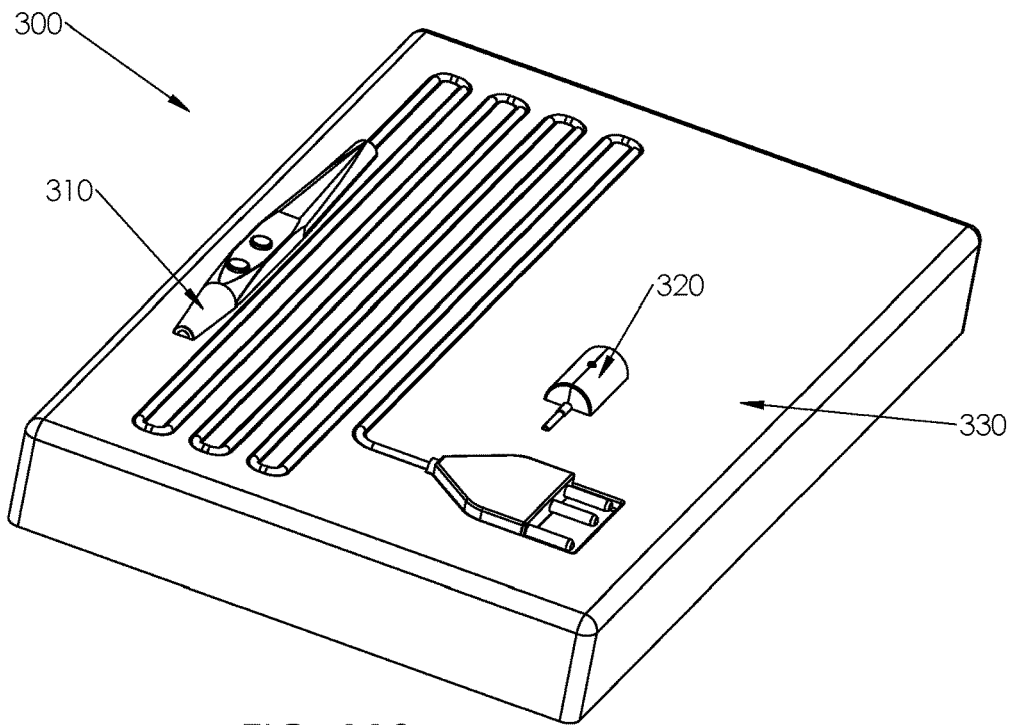
FIG. 110 is a perspective view of a kit with a packaging enclosure containing the lighted blade assembly of FIG. 106 and an electrocautery instrument.
Figure 111:
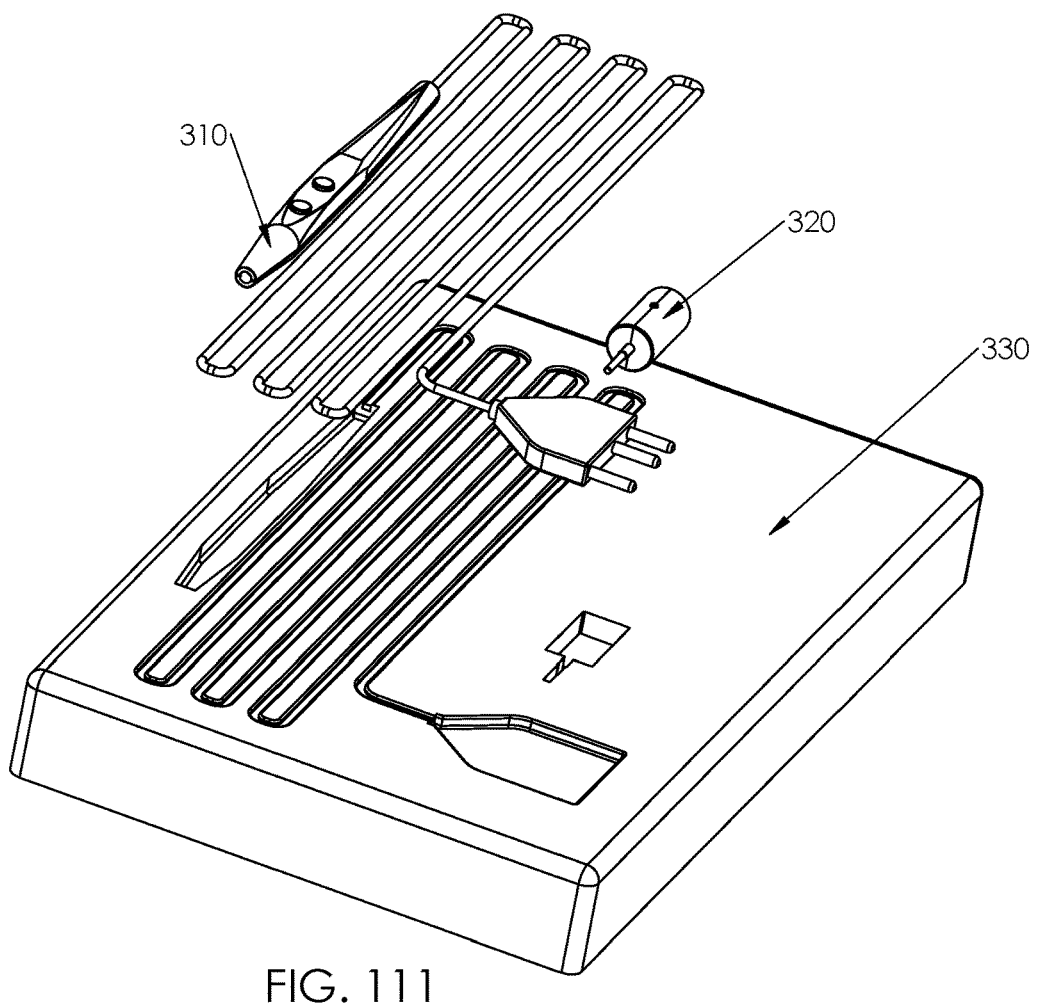
FIG. 111 is an exploded perspective view of the kit shown in FIG. 110.
Figure 112:
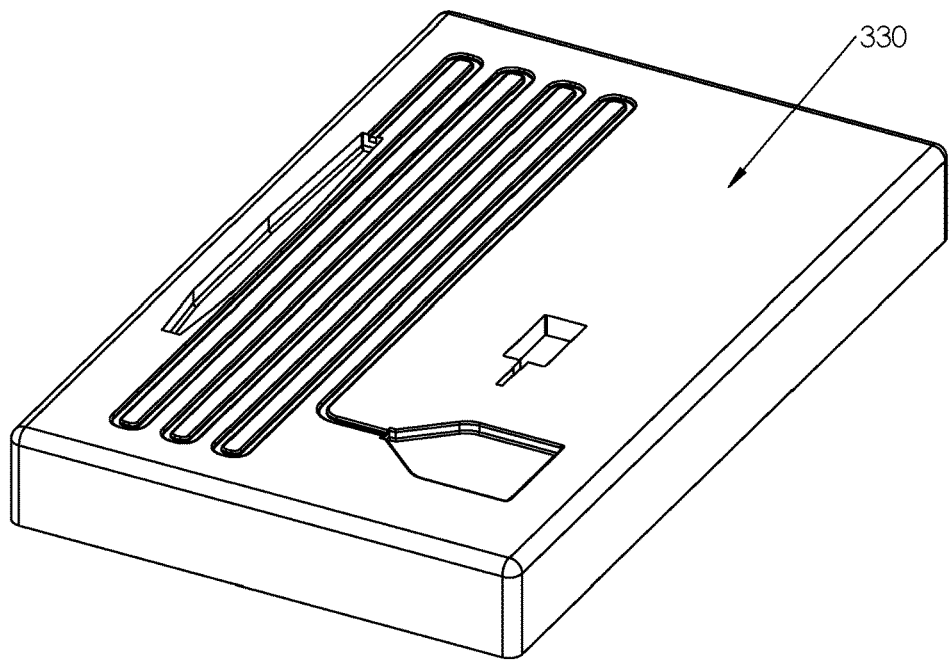
FIGS. 112 and 113 are top and bottom perspective views of the packaging enclosure for the kit shown in FIG. 110.
Figure 113:
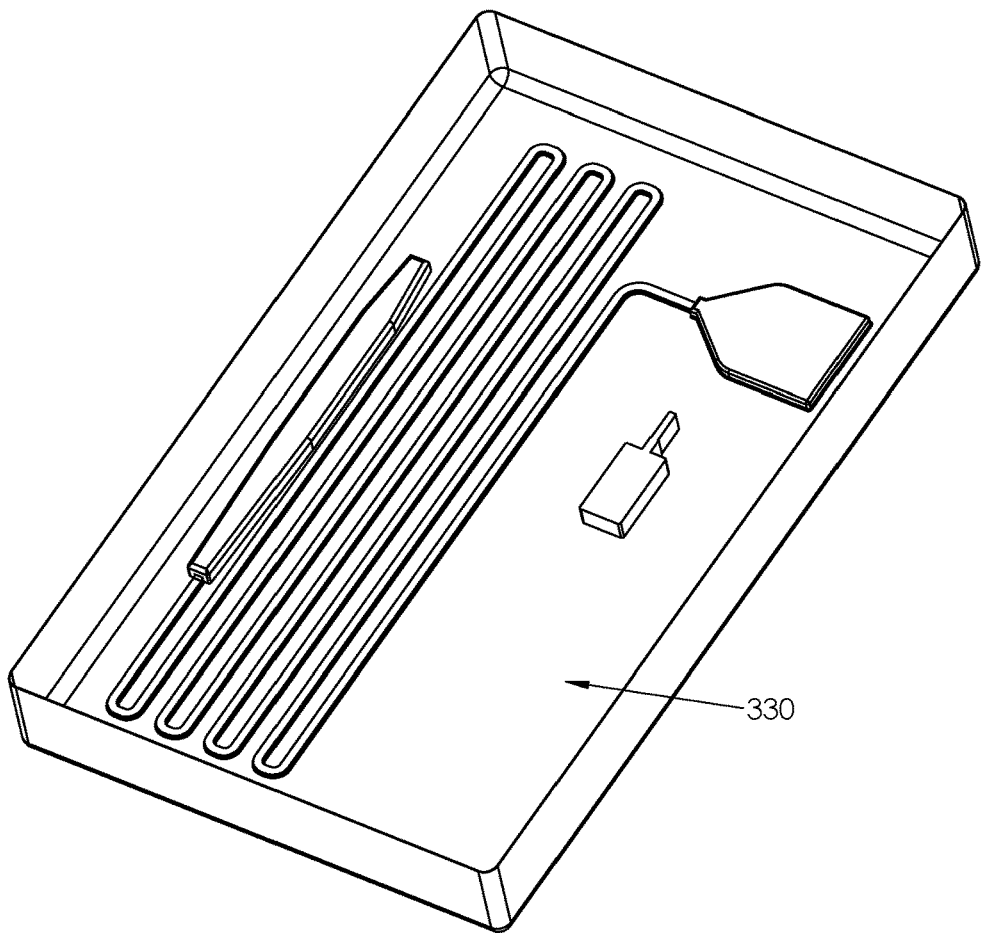

The lighted electrocautery blade assembly 140 further includes an elongated electrode adapter 210 that is mounted within the housing 202, 202' and includes a distal reception portion 216, a medial body portion 215 and a proximal connector portion 206. The distal reception portion 216 of electrode adapter 210 is located within the distal end portion of the housing 202, 202' for receiving an electrocautery blade 150, as shown in FIG. 105. This is in contrast to the embodiment of the invention shown in FIG. 44, wherein the distal reception portion 74 of the electrode adapter 75 extends axially from the distal end of the housing 66, 68 to receive an electrocautery blade end effector 60.

Figure 104:
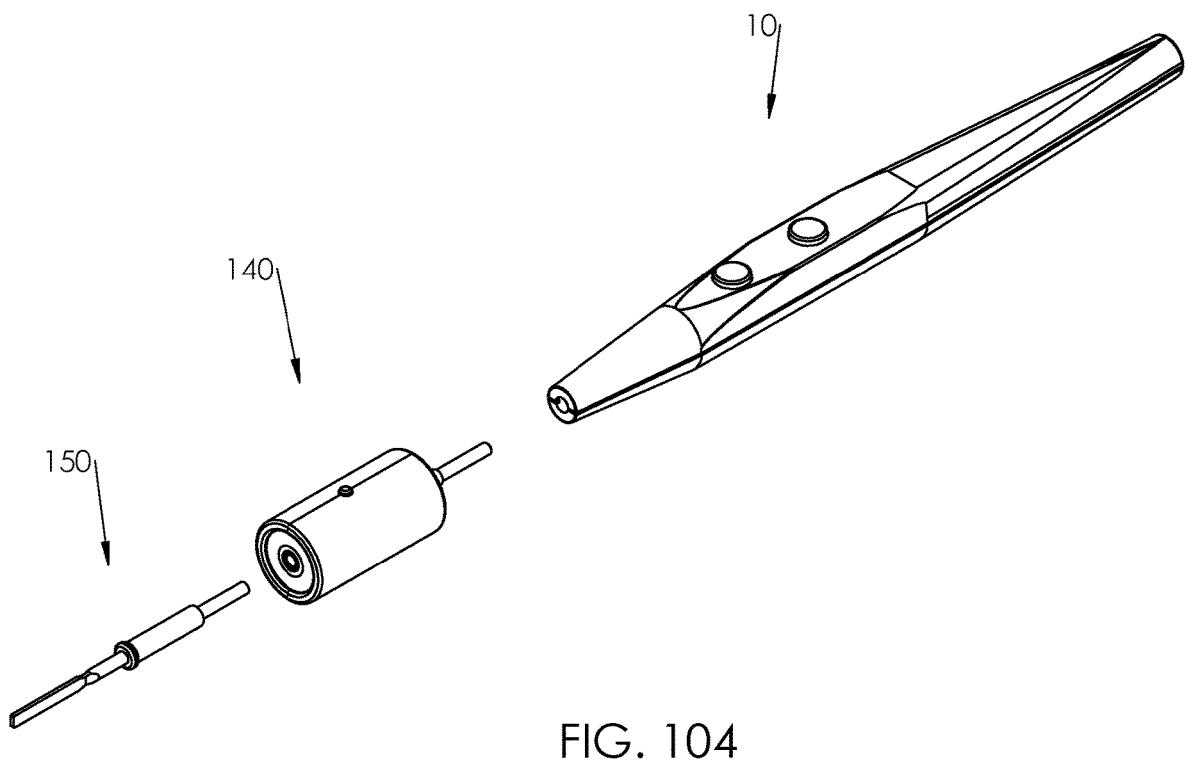
FIG. 104 is a perspective view of another embodiment of the lighted blade assembly of the subject invention before it is assembled and attached to the distal end portion of a surgical instrument.

In this embodiment of the invention, the medial body portion 215 of electrode adapter 210 is provided with an insulating sheath 217 and it includes a rectangular flange 208 for engagement within a complementary recess 208' formed in the housing 202, 202' for securing the axial position of the electrode adapter 210. The proximal connector portion 206 of electrode adapted 210 extends from the proximal end of the housing 202, 202' for electrically coupling with a surgical instrument 10, as shown in FIGS. 104 and 105.

Referring to FIGS. 110 through 113, the subject invention is also directed to a kit for performing a surgical procedure, which is designated generally by reference numeral 300. The kit 300 includes a preformed packaging enclosure 330 that contains a handheld electrosurgical instrument 310 configured for connection to a source of RF energy, and a lighted electrocautery blade assembly 320 for attachment to the handheld electrosurgical instrument 310 and powered by at least one internal battery cell. As shown, the lighted blade assembly in kit 300 is of the type illustrated in FIG. 106, although the kit could include any one of the various lighted blade assemblies disclosed herein.

Figure 114:
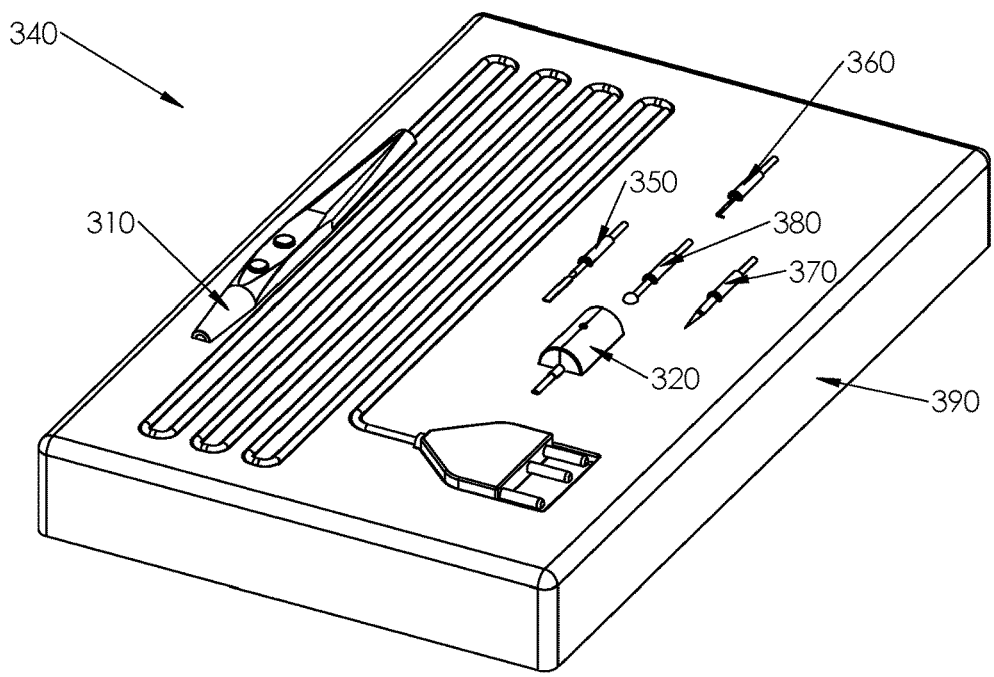
FIG. 114 is a perspective view of another kit with a packaging enclosure containing the lighted blade assembly of FIG. 106, an electrocautery instrument and different types of electrode blades for use with the assembly.
Figure 115:
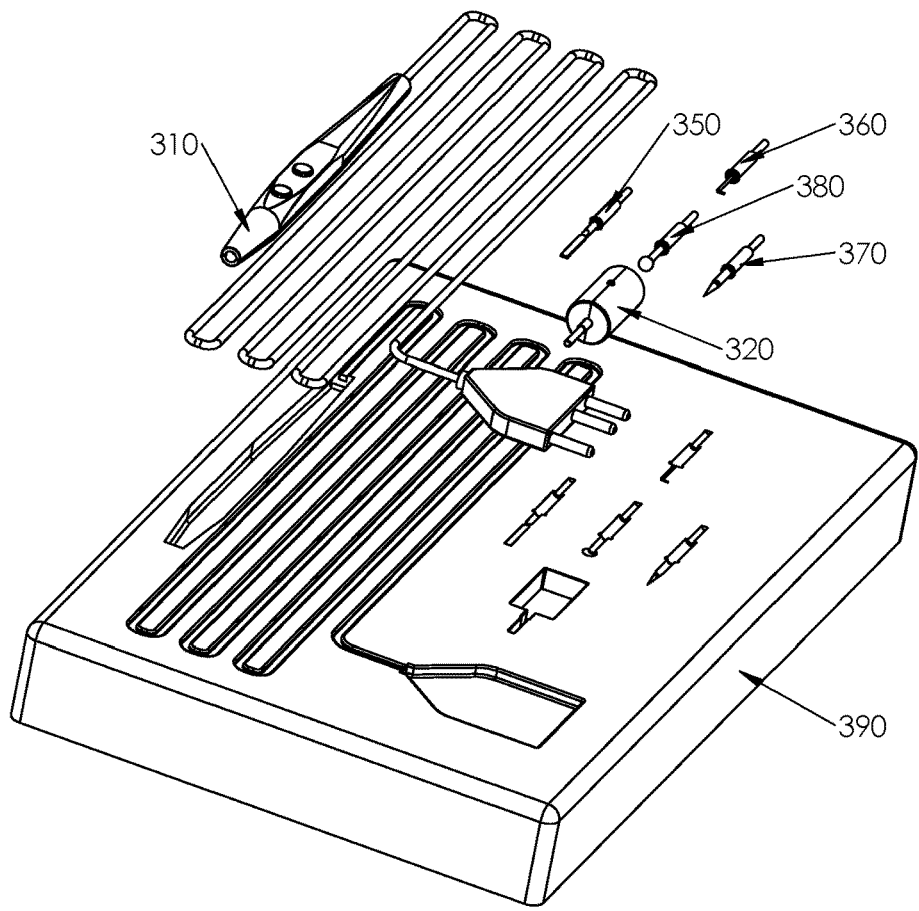
FIG. 115 is an exploded perspective view of the kit shown in FIG. 114.

Referring to FIGS. 114 and 115, there is illustrated another kit designated generally by reference numeral 340, which includes a preformed packaging enclosure 390 that contains a handheld electrosurgical instrument 310 configured for connection to a source of RF energy, a lighted electrocautery blade assembly 320 (e.g., the lighted blade assembly shown in 7 106) for attachment to the handheld electrosurgical instrument 310 and powered by at least one internal battery cell, and plurality of different electrode blade attachments, including a blade electrode 350, a hook electrode 360, a needle electrode 370 and a ball electrode 380. It is envisioned that the kit 340 could alternatively include a plurality of identical electrode blade attachments, or the kit could include a plurality of electrode blades that are of different lengths.

While the subject disclosure has been shown and described with reference to preferred embodiments, those skilled in the art will readily appreciate that changes or modifications may be made thereto without departing from the spirit or scope of the subject disclosure.

What is claimed is:

1. A lighted electrocautery blade assembly for attachment to a handheld electrosurgical instrument comprising:
   a) an elongated housing having an LED light assembly as a distal end thereof for illuminating a surgical site; and
   b) an electrode having a medial portion extending through and mounted within the elongated housing such that a distal end portion of the electrode extends from the distal end of the elongated housing to define an electrocautery blade and a proximal end portion of the electrode extends from a proximal end wall of the housing to define a connector for electrically coupling with the electrosurgical instrument, wherein the LED light assembly includes a plurality of LED light sources supported on an annular printed circuit board that surrounds the electrocautery blade and is powered by at least one battery cell located within the housing, and the electrode is powered by an RF energy source connected to the electrosurgical instrument, wherein a flange surrounds the medial portion of the electrode for engaging a complementary recess formed within the proximal end wall of the housing for mounting the electrode within the housing, wherein the proximal end wall of the housing is configured to abut against a distal end of the handheld electrosurgical instrument when the connector is electrically coupled with the handheld electrosurgical instrument, and wherein the at least one battery cell is controlled by an actuation switch that is electrically connected to the annular printed circuit board of the LED light assembly and extends outwardly from the proximal end wall of the housing so as to interact with the distal end of the handheld surgical instrument when the lighted electrocautery blade assembly is attached thereto.

2. A lighted electrocautery blade assembly as recited in claim 1, wherein the LED light assembly is defined by a plurality of battery cells supported within the elongated housing.

3. A lighted electrocautery blade assembly as recited in claim 1, wherein the at least one battery cell is charged by the RF energy source.

4. A lighted electrocautery blade assembly as recited in claim 1, wherein the medial portion of the electrode is sheathed in an electrically insulating sleeve.

5. A lighted electrocautery blade assembly as recited in claim 4, wherein the flange is formed integral with the medial portion of the electrode and is rectangular to prevent axial rotation of the electrode relative to the housing.

6. A lighted electrocautery blade assembly as recited in claim 1, wherein a lens is positioned in front of the LED light assembly.

* * * * *